(12) United States Patent
Lee et al.

(10) Patent No.: US 11,996,182 B2
(45) Date of Patent: May 28, 2024

(54) APPARATUS AND METHOD FOR MEDICAL IMAGE READING ASSISTANT PROVIDING REPRESENTATIVE IMAGE BASED ON MEDICAL USE ARTIFICIAL NEURAL NETWORK

(71) Applicants: Coreline Soft Co., Ltd., Seoul (KR); THE ASAN FOUNDATION, Seoul (KR); UNIV. OF ULSAN FOUNDATION FOR INDUSTRY COOPERATION, Ulsan (KR)

(72) Inventors: Sang Min Lee, Seoul (KR); Dong Hyun Yang, Seoul (KR); Jin Kook Kim, Seoul (KR); Jaeyoun Yi, Seoul (KR); Donghoon Yu, Gimpo-si (KR); Seung Lee Park, Seoul (KR)

(73) Assignees: CORELINE SOFT CO., LTD., Seoul (KR); THE ASAN FOUNDATION, Seoul (KR); UNIV. OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 794 days.

(21) Appl. No.: 16/953,175

(22) Filed: Nov. 19, 2020

(65) Prior Publication Data

US 2021/0151171 A1  May 20, 2021

(30) Foreign Application Priority Data

Nov. 19, 2019  (KR) .................. 10-2019-0148489

(51) Int. Cl.
*G06K 9/00* (2022.01)
*G06F 3/0482* (2013.01)
(Continued)

(52) U.S. Cl.
CPC .......... *G16H 30/40* (2018.01); *G06F 3/0482* (2013.01); *G06N 3/08* (2013.01); *G06T 7/0012* (2013.01);
(Continued)

(58) Field of Classification Search
CPC ........ G16H 30/40; G16H 30/20; G16H 50/20; G16H 50/70; G16H 70/20; G06F 3/0482;
(Continued)

(56) References Cited

U.S. PATENT DOCUMENTS 8,165,368 B2   4/2012  Vijaykalyan et al.
8,923,580 B2  12/2014  Dekel et al.
(Continued)

FOREIGN PATENT DOCUMENTS

JP      2008-188214 A    8/2008
KR   10-2014-0091176 A   7/2014
(Continued)

*Primary Examiner* — Xin Jia
(74) *Attorney, Agent, or Firm* — United One Law Group LLC; Kongsik Kim; Jhongwoo Peck

(57) ABSTRACT

Disclosed is an apparatus for assisting the reading of a medical image based on a medical artificial neural network, the apparatus including a computing system. An apparatus according to an embodiment of the present invention includes a computing system, and the computing system includes at least one processor. The at least one processor acquires or receives a first analysis result obtained through the inference of a first artificial neural network for a first medical image, generates a first visualization format, which is a representative visualization format of the first medical image, based on the first analysis result, and visualizes the first medical image and the first analysis result based on the first visualization format.

19 Claims, 15 Drawing Sheets

(51) Int. Cl.
  *G06N 3/08* (2023.01)
  *G06T 7/00* (2017.01)
  *G06T 7/11* (2017.01)
  *G06T 11/00* (2006.01)
  *G16H 30/20* (2018.01)
  *G16H 30/40* (2018.01)
  *G16H 50/20* (2018.01)

(52) U.S. Cl.
  CPC ............... *G06T 7/11* (2017.01); *G06T 11/00* (2013.01); *G16H 30/20* (2018.01); *G16H 50/20* (2018.01); *G06T 2200/24* (2013.01); *G06T 2207/20081* (2013.01); *G06T 2207/20084* (2013.01); *G06T 2207/20092* (2013.01); *G06T 2207/30061* (2013.01); *G06T 2207/30096* (2013.01)

(58) Field of Classification Search
  CPC .......... G06N 3/08; G06N 3/045; G06N 3/063; G06T 7/0012; G06T 7/11; G06T 11/00; G06T 2200/24; G06T 2207/20081; G06T 2207/20084; G06T 2207/20092; G06T 2207/30061; G06T 2207/30096; G06T 2207/10081

See application file for complete search history.

(56) References Cited

U.S. PATENT DOCUMENTS

| | | |
|---|---|---|
| 9,773,305 B2 | 9/2017 | Lee et al. |
| 10,445,462 B2 | 10/2019 | Sorenson et al. |
| 2020/0211692 A1* | 7/2020 | Kalafut ................. G06N 20/00 |

FOREIGN PATENT DOCUMENTS

| | | | | |
|---|---|---|---|---|
| KR | 10-1684998 B1 | 12/2016 | | |
| KR | 10-1818074 B1 | 1/2018 | | |
| KR | 10-1938992 B1 | 1/2019 | | |
| KR | 10-1943011 B1 | 1/2019 | | |
| KR | 20190060606 A | * 6/2019 | ............. | G06N 20/00 |
| KR | 10-2019-0105210 A | 9/2019 | | |
| KR | 10-2019-0117187 A | 10/2019 | | |
| WO | WO-2019117563 A1 | * 6/2019 | ........... | A61B 5/0022 |

* cited by examiner

APPARATUS AND METHOD FOR MEDICAL IMAGE READING ASSISTANT PROVIDING REPRESENTATIVE IMAGE BASED ON MEDICAL USE ARTIFICIAL NEURAL NETWORK

CROSS-REFERENCE TO RELATED APPLICATIONS

This application claims priority to Korean Patent Application No. KR10-2019-0148489, filed on Nov. 19, 2019. The entire contents of which is incorporated herein by reference in its entirety.

TECHNICAL FIELD

The present invention relates to an apparatus and method for assisting the reading of a medical image of a subject. More particularly, the present invention relates to a computing system for assisting the reading of a medical image using an analysis result of a medical artificial neural network and software that is executed in the computing system.

The present invention was derived from the research conducted as part of the Fundamental Software (SW) Computing Technology Development Project sponsored by the Korean Ministry of Science and ICT and the Institute for Information and Communications Technology Promotion (Project Management Number: 2018-0-00861; and Project Name: Development of Intelligent SW Technology for Analysis of Medical Data).

BACKGROUND ART

Currently, medical images such as computed tomography (CT) images are widely used to analyze lesions and use analysis results for diagnosis. For example, chest CT images are frequently used for reading because they enable readers to observe abnormalities in parts of the human body, such as the lungs, the bronchi, and the heart.

Some of the findings that can be read through chest CT images may be easily overlooked by human doctors because they are not easy to read and even radiologists can distinguish their features and forms only after years of training. In particular, when the level of difficulty in reading is high as in the reading of a lung nodule, the case of overlooking a lesion may occur even when a doctor pays a high degree of attention, which may lead to trouble.

In order to assist in reading images that humans can easily overlook, the need for computer-aided diagnosis (CAD) has arisen. Conventional CAD technology is limited to assisting doctors in making decisions in significantly limited areas. For example, Korean Patent Application Publication No. 10-2014-0091176 and U.S. Pat. No. 9,773,305 disclose a conventional apparatus and method for assisting the diagnosis of lesions.

The reading of a lesion using CAD may include the process of identifying a suspected lesion first and then evaluating a score (e.g., confidence, malignity, or the like) for that region. For example, if a plurality of nodules is found in the lungs, it will be necessary to specify a nodule that is expected to have the highest malignity and to determine a future treatment plan.

Meanwhile, since there is a plurality of nodules, it is not known until reading which of the nodules is the most malignant. Accordingly, there frequently occurs a case where diagnosis is performed from a nodule whose actual malignity is not high or which is not expected to be highly malignant and thus the efficiency of reading is degraded. It is also difficult to know which nodule is a real nodule before reading and reliability is low. Accordingly, when the diagnosis is performed from a portion that is not expected to be an actual nodule, the efficiency of reading is also deteriorated.

Korean Patent No. 10-1943011 entitled "Method for Supporting Reading of Medical Image of Subject and Apparatus using the Same" proposes a method that introduces a score evaluation method into a conventional lesion detection system and allow a lesion with a higher score (e.g., confidence, malignancy, or the like) among detected lesions can be read first, thereby increasing the efficiency of reading, and also proposes an apparatus using the same.

Korean Patent No. 10-1943011 discloses technology in which when a number of lesions are detected for a single type of disease, a list in which entries are arranged from a lesion having the highest score, such as reliability, malignancy or the like, within a single display setting is displayed, and an image related to a selected lesion is displayed when a user selects the lesion from the list. Korean Patent No. 10-1943011 assumes a case where a plurality of types of lesions is detected for a single type of disease, and thus it does not propose a method corresponding to a case where lesions for a plurality of types of diseases are detected.

Furthermore, Korean Patent No. 10-1938992 entitled "CAD System and Method for Generating Description of Reason for Diagnosis" introduces a technology that generates a feature vector by concatenating pieces of feature information extracted based on a DNN and a GAN in order to derive basis information for the diagnosis of a lesion. However, according to the technology of Korean Patent No. 10-1938992, an artificial neural network only extracts descriptive information based on the similarity between a detected feature within an image and a diagnosis result, and the relevance between the extracted descriptive information and the diagnosis result is calculated only within the artificial neural network. Accordingly, since there is no verification of whether the descriptive information extracted by the technology of Korean Patent No. 10-1938992 is clinically useful information, there is little evidence that a human can recognize it as a description of the diagnosis result of the artificial neural network.

As to recent medical images such as computed tomography (CT) or magnetic resonance image (MRI) images, a series of medical images is acquired through a single acquisition process, and the series of medical images is not limited to a single type of lesion but may also be used to detect various types of lesions.

When a clinician or radiologist desires to identify various types of lesions on a single series of medical images, it is necessary to improve the clinician or radiologist's workflow and hanging protocol. The hanging protocol refers to display settings for medical images.

There have been many prior arts intended to improve workflows and hanging protocols. For example, U.S. Pat. No. 8,165,368 entitled "Systems and Methods for Machine Learning Based Hanging Protocols" and U.S. Pat. No. 8,923,580 entitled "Smart PACS Workflow Systems and Methods Driven by Explicit Learning from Users" propose the technology that provides user-specific hanging protocols by learning a user's preference or a user's past display manipulation process.

Although the technologies of the prior art documents may optimize workflows and hanging protocols based on a user preference, a body part from which a medical image is acquired, and a past medical history, they do not propose a workflow and a hanging protocol based on diagnostic information or lesion information included in a currently provided medical image.

SUMMARY

As to recent medical images such as CT or MRI images, a series of medical images is acquired through a single acquisition process, and the series of medical images is not limited to a single type of lesion but may also be used to detect various types of lesions. For example, for the lungs, a lung nodule as well as chronic obstructive pulmonary disease (COPD) may be diagnosed, emphysema may be diagnosed, and/or chronic bronchitis and/or an airway-related disease may also be diagnosed.

If a clinician or radiologist is provided with only a diagnostic list of lesions as in the prior art, the clinician or radiologist needs to select each lesion from the list and find and execute display settings appropriate for the lesion. In this case, a problem arises in that the time required to execute or wait for the work that is not directly related to reading increases and thus the efficiency of a workflow is degraded.

If a clinician or radiologist can devote time only to the work that is directly related to reading, it will shorten the reading time and increase the efficiency of a workflow.

An object of the present invention is to shorten the reading time and increase the efficiency of a workflow so that a clinician or radiologist can spend time only for the work that is directly related to reading based on analysis results based on medical images in an environment equipped with artificial intelligence capable of performing the analysis of a number of functions on medical images.

An object of the present invention is to provide a user interface and display environment that improve the efficiency of reading, assist a clinician or radiologist in deriving a more accurate diagnosis result within a short period of time, and increase the accuracy of analysis.

Meanwhile, with the recent development of artificial intelligence technology, the field of application of artificial intelligence has been expanding from conventional diagnosis and lesion detection to a variety of means for obtaining analysis and quantitative information on specific regions in the medical imaging field. In this case, there is a demand for a menu that enables a medical professional to perform clinical judgment and decision-making on the artificial intelligence-based analysis result and quantitative information of medical images by providing a representative visualization format for the analysis result and quantitative information of medical images. In response to such demand, an object of the present invention is to provide a representative visualization format that facilitates clinical judgment and decision-making for the results of the artificial intelligence-based analysis and quantification of medical images.

Meanwhile, the artificial intelligence-based analysis results and quantification results of medical images are derived through preprocessing such as image segmentation.

In this case, if there is an error in the preprocessing process in terms of the workflow, a subsequent analysis process includes the error. Accordingly, there is a demand for a menu that allows a medical professional to perform clinical judgment and decision-making on analysis results by presenting both the analysis results on medical images and the results of a preprocessing process for deriving the analysis results of the medical images in terms of the workflow. The present invention is intended to respond to this demand, and an object of the present invention is to visualize the results of the artificial intelligence-based analysis and quantification of medical images and also visualize preprocessing results obtained to provide the analysis and quantification results in terms of a workflow, thereby assisting a medical professional in performing clinical judgment and decision-making.

An object of the present invention is to, when a medical professional rejects artificial intelligence-based analysis and quantification results, allow the medical professional to reject preprocessing results that are the basis for the derivation of the artificial intelligence-based analysis and quantification results and also provide a user menu that allows a preprocessing process, an analysis process, and a quantification process to be performed again independently of artificial intelligence.

According to an aspect of the present invention, there is provided a medical image reading assistance apparatus for assisting the reading of a medical image based on a medical artificial neural network, the medical image reading assistance apparatus including a computing system, wherein the computing system includes at least one processor. The at least one processor is configured to: acquire or receive a first analysis result obtained through the inference of a first artificial neural network for a first medical image; generate a first visualization format, which is a representative visualization format of the first medical image, based on the first analysis result; and visualize the first medical image and the first analysis result based on the first visualization format.

The at least one processor may be further configured to provide a first user menu adapted to receive information about a user's approval for the first analysis result visualized based on the first visualization format. The first user menu may be provided as a user interface adapted to allow the user to select either "Confirm" or "Reject."

The at least one processor may be further configured to, when the user does not approve the first analysis result, provide a second user menu adapted to generate a second analysis result corresponding to the first analysis result for the first medical image independently of the first analysis result.

The at least one processor may be further configured to, when the user approves the first analysis result, store the first analysis result in a database in association with the first medical image.

The at least one processor may be further configured to visualize the first analysis result by overlaying the first analysis result on the first visualization format of the first medical image.

The at least one processor may be further configured to generate the first visualization format based on the first medical image and the first analysis result so that the first analysis result is included in the first visualization format.

The at least one processor may be further configured to generate the first visualization format based on at least one of the image segmentation of the first medical image, clinical diagnosis, and the quantitative measurement result of a segmented object within the first medical image included in the first analysis result.

The first visualization format may include at least one of at least one view of the first medical image, at least part of the first medical image selected from the first medical image based on the relevance to the first analysis result, and the reconstruction of the first medical image; and the first analysis result may be visualized such that the first analysis result is distinguished based on quantitative information included in the first analysis result.

The first artificial neural network may provide at least one of the image segmentation of the first medical image, clinical diagnosis, and the quantitative measurement result of a segmented object within the first medical image as the first analysis result.

The computing system may further include a second artificial neural network formed as an artificial neural network that has received a plurality of second visualization formats selected by a professional for a plurality of third analysis results obtained for a plurality of second medical images and has learned a function of generating visualization formats based on the relevance between the plurality of third analysis results and the plurality of second visualization formats. The at least one processor may be further configured to input the first analysis result to the second artificial neural network and control the second artificial neural network so that the first visualization format is acquired through the inference of the second artificial neural network.

The computing system may further include a communication interface configured to transmit and receive data to and from the first artificial neural network disposed outside the computing system. The at least one processor may be further configured to acquire or receive the first analysis result obtained through the inference of the first artificial neural network for the first medical image via the communication interface.

The computing system may further include a communication interface configured to transmit and receive data to and from the database disposed outside the computing system. The at least one processor may be further configured to store the first analysis result in the database in association with the first medical image via the communication interface.

According to another aspect of the present invention, there is provided a medical image reading assistance method that is performed by a computing system, wherein the computing system comprises at least one processor. The method includes: acquiring or receiving, by the at least one processor, a first analysis result obtained through the inference of a first artificial neural network for a first medical image; generating, by the at least one processor, a first visualization format, which is a representative visualization format of the first medical image, based on the first analysis result; and visualizing, by the at least one processor, the first medical image and the first analysis result based on the first visualization format.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Other objects and features of the present invention in addition to the above-described objects will be apparent from the following description of embodiments with reference to the accompanying drawings.

Embodiments of the present invention will be described in detail below with reference to the accompanying drawings. In the following description, when it is determined that a detailed description of a related known component or function may unnecessarily make the gist of the present invention obscure, it will be omitted.

Deep learning/CNN-based artificial neural network technology, which has recently developed rapidly, is considered for the purpose of identifying a visual element that is difficult to identify with the human eye when it is applied to the imaging field. The fields of application of the above technology are expected to expand to various fields such as security, medical imaging, and non-destructive testing.

For example, in the medical imaging field, there are cases where a tissue in question is not immediately diagnosed as a cancer tissue in a biopsy state but whether it is a cancer tissue is determined only after being monitored from a pathological point of view. Although it is difficult to confirm whether a corresponding cell is a cancer tissue in a medical image with the human eye, there is an expectation that the application of artificial neural network technology may acquire more accurate prediction results than observation with the human eye.

It is expected that this artificial neural network technology is applied and performs the analysis process of detecting a disease or lesion difficult to identify with the human eye in a medical image, segmenting a region of interest such as a specific tissue, and measuring the segmented region.

The present invention is directed to a medical image reading assistance system that provides a configuration that visualizes various analysis techniques, to which such artificial neural network technology is applied, in the most appropriate form for that can be read by a human professional.

Figure 1:
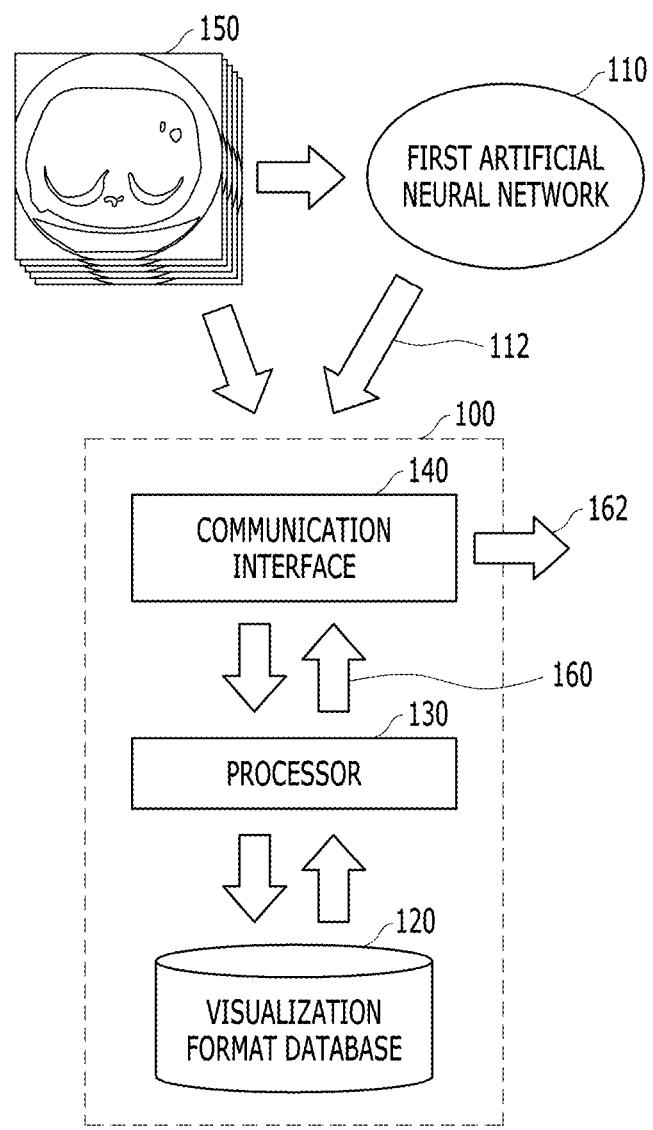
FIG. 1 is a diagram showing a medical image reading assistance apparatus that provides a representative image based on an analysis result of a medical artificial neural network according to an embodiment of the present invention.

FIG. 1 is a diagram showing a medical image reading assistance apparatus that provides a representative image based on an analysis result of a medical artificial neural network according to an embodiment of the present invention.

Referring to FIG. 1, the medical image reading assistance apparatus according to the present embodiment includes a computing system 100. The computing system 100 includes at least one processor 130. The computing system 100 may further include a visualization format database 120. The at least one processor 130 acquires or receives a first analysis result 112 obtained through the inference of a first artificial neural network 110 for a first medical image 150, generates a first visualization format 160, which is a representative visualization format of the first medical image 150, based on the first analysis result 112 in cooperation with the visualization format database 120, and generates visualization information 162 in which the first medical image 150 and the first analysis result 112 are displayed on a screen based on the first visualization format 160.

The first visualization format 160 may be generated in a format most appropriate to assist the reading of the first medical image 150, such as a visualization format wherein a user, who is a medical professional, can check easily the organs, anatomical structures, and/or the segmented regions at a glance. The first visualization format 160 may also vary depending on the first analysis result 112 of the first medical image 150. The first visualization format 160 is generated based on the first medical image 150 and the first analysis result 112. The first visualization format 160 may be derived in an appropriate form for a medical professional, who is a user, to judge the first analysis result 112 or to make a decision on the first analysis result 112.

Based on the type of the first analysis result 112, the analysis content included in the first analysis result 112, and/or quantification information, the types of appropriate first visualization formats 160 may be extracted in advance and stored in the visualization format database 120. In this case, after receiving the first analysis result 112, the processor 130 may request data from the visualization format database 120 based on the analysis content included in the first analysis result 112 and the content of the first medical image 150 to which the first analysis result 112 is related. The visualization format database 120 may transfer visualization format information corresponding to the first analysis result 112 and the first medical image 150 to the processor 130 in response to the request from the processor 130. The processor 130 may generate a visualization format appropriate for the first analysis result 112 and the first medical image 150 based on the visualization format information received from the visualization format database 120, may generate a first visualization format 160 by applying the visualization format to the first medical image 150, and may transmit the first visualization format 160 to the communication interface 140. The process of receiving the visualization format information from the visualization format database 120 and generating the first visualization format 160 may be performed in a rule-based manner. The at least one processor 130 may provide a first user menu capable of receiving information about a user's approval for the first analysis result 112 displayed on the screen based on the first visualization format 160. The first user menu may be provided as a user interface adapted to allow the user to select either "Confirm" or "Reject."

When the user does not approve the first analysis result 112, the at least one processor 130 may provide a second user menu adapted to generate a second analysis result corresponding to the first analysis result 112 for the first medical image 150 independently of the analysis result 112. The second user menu may be a menu that may generate a second analysis result that replaces the first analysis result 112. The second user menu may be a menu that may manually or semi-automatically generate the second analysis result, and may be a user menu that may be partially automatically executed, receive user input intermittently and interactively, generate the second analysis result, and replace the first analysis result 112 with the second analysis result. In addition, when the user does not approve the first analysis result 112, there may be provided a user menu adapted to allow the user to independently generate a preprocessing result that is the basis for the generation of the first analysis result 112. The preprocessing result may also be generated manually or semi-automatically by the user menu.

The computing system 100 may further include a communication interface 140 configured to transmit and receive data to and from the first artificial neural network 110 disposed outside the computing system 100. The at least one processor 130 may acquire or receive the first analysis result 112 obtained through the inference of the first artificial neural network 110 for the first medical image 150 via the communication interface 140.

In FIG. 1, there is shown an embodiment in which the first artificial neural network 110 is located outside the computing system 100. The process of connecting to a location outside the computing system 100 is performed via the communication interface 140. Accordingly, the at least one processor 130 may receive the first analysis result 112, generated by the first artificial neural network 110, via the communication interface 140, and may receive or acquire the first medical image 150 via the communication interface 140. The first visualization format 160 generated by the processor 130 is combined with the first medical image 150 and/or the first analysis result 112 to be generated as visualization information 162 and be transferred to a display (not shown) outside the computing system 100 via the communication interface 140. The process of generating the visualization information 162 based on the first visualization format 160 may be performed by the processor 130, or may be performed by the communication interface 140 under the control of the processor 130.

According to an embodiment of the present invention, the first visualization format 160 may include the reconstruction or reformatting of the first medical image 150, for example, a 3D volume rendered image a segmentation result based on the pre-processing is applied thereto, and Axial/Coronal/Sagittal images the segmentation result based on the pre-processing is overlaid thereon. In this case, according to the type of the first analysis result 112, the at least one processor 130 may generate the visualization information 162 by overlaying the first analysis result 112 on the first visualization format 160 of the first medical image 150 and perform visualization. For example, when the first analysis result 112 is an analysis result related to the detection or diagnosis of a lesion, the first analysis result 112 and/or a pre-processed result such as segmented region may be overlaid on the first visualization format 160 of the first medical image 150.

According to another embodiment of the present invention, the first visualization format 160 may include the reconstruction or reformatting of the first medical image 150. Depending on the type of the first analysis result 112, the first visualization format 160 may be generated such that the first analysis result 112 together with the first medical image 150 is included in the first visualization format 160.

In this case, the at least one processor 130 may generate the first visualization format 160 based on the first medical image 150 and the first analysis result 112 so that the first analysis result 112 is included in the first visualization format 160. For example, the first analysis result 112 is an analysis result related to the segmentation and quantification of an airway, and the segmentation of an airway is required as a preprocessing process. In this case, the first visualization format 160 may be generated such that the first analysis result 112 and the preprocessing result are included in the first visualization format 160 together. A quantification result, which is the first analysis result 112, may be visualized together with a 3D volume rendering image of the first medical image 150 by representing the result of the segmentation of the airway of the first medical image 150, which is a preprocessing result, as the 3D volume rendering image and adding a visualization element such as color, brightness, saturation, and/or pattern to the 3D volume rendering image. In this case, the first visualization format 160 may include the 3D volume rendering image of the first medical image 150 and the visualization element added thereto. In this case, the first visualization format 160 may be derived as a representative visualization format capable of visualizing the information of the first medical image 150, the preprocessing result, and the first analysis result 112 together.

The at least one processor 130 may generate the first visualization format 160 based on at least one of the image segmentation of the first medical image 150 included in the first analysis result 112, clinical findings, clinical diagnosis, and the result of the quantitative measurement of a segmented object within the first medical image 150. The at least one of the type of disease, the type of lesion, the type of clinical findings, the type of clinical diagnosis, and the result of the quantitative measurement of the lesion detected in the first medical image 150 may affect, as context information, the process in which the processor 130 generates the first visualization format 160, where the context information includes information about the pre-processing related to the generation of the first analysis result 112, for example, a segmentation result about organs, lesions, and/or anatomical structures.

The first visualization format 160 may include at least one view of the first medical image 150, at least part of the first medical image 150 selected from the first medical image 150 based on the relevance to the first analysis result 112, the reconstruction of the first medical image 150, and the reformatting of the first medical image 150. The first analysis result 112 may be visualized such that it can be distinguished based on the quantitative information included in the first analysis result 112.

The first artificial neural network 110 may provide at least one of the image segmentation of the first medical image 150, clinical diagnosis, and the result of the quantitative measurement of a segmented object within the first medical image 150 as the first analysis result 112.

The first visualization format 160 may include settings for at least one view of the first medical image 150 related to the first analysis result 112, a menu adapted to display the first analysis result 112 in the first medical image 150, the layout of at least one view of the first medical image 150, and a user menu adapted such that the user can respond to the first analysis result 112 displayed in the first medical image 150 therein. Display settings similar to the first visualization format 160 and specialized in the medical field are also called a hanging protocol. The first visualization format 160 is not the same as the hanging protocol, and the first visualization format 160 is not limited to the hanging protocol but may include all of an image-processed view of the first medical image 150, and volume-rendered, reconstructed and reformatted images in order to appropriately display the first analysis result 112.

More specifically, the hanging protocol may include settings for a plurality of views of the first medical image 150 related to the first analysis result 112, a visualized menu adapted to display the first analysis result 112 within at least one of the plurality of views of the first medical image 150, a visualized menu adapted to display a related portion in the first medical image 150 that is clinically related to the first analysis result 112, the layout of the plurality of views of the first medical image 150, a visual/auditory representation adapted such that the first analysis result 112 and a related portion within the first medical image 150 clinically correlated with the first analysis result 112 are synchronized with each other between the plurality of views of the first medical image 150, and a user menu adapted to allow a user to respond to the first analysis result 112 displayed in at least one of the plurality of views of the first medical image 150 and/or a related portion having clinical relevance to the first analysis result 112 displayed in the first medical image 150. For general information about the hanging protocol, refer to the above-described U.S. Pat. No. 8,165,368 entitled "Systems and Methods for Machine Learning Based Hanging Protocols" and U.S. Pat. No. 8,923,580 entitled "Smart PACS Workflow Systems and Methods Driven by Explicit Learning from Users."

At least part of such a hanging protocol may be included in the first visualization format 160 within a range that can support a user's judgment and decision-making on the first analysis result 112. However, the first visualization format 160 may be a view, a reconstructed image, or a reformatted image specialized for the display of the first analysis result 112 or the preprocessing result thereof within a given hanging protocol. In this case, the first visualization format 160 may further include various detailed visualization formats that are not defined in the hanging protocol.

The processor 130 may generate the first visualization format 160 based on the rules for generating visualization formats stored in the visualization format database 120. In other words, the first analysis result 112 or the main features of the first analysis result 112 may be extracted and then a query may be sent to the visualization format database 120 based on the extracted information. In response to the query, the visualization format database 120 may provide a hanging protocol response related to the query to the processor 130 based on the rules stored in the visualization format database 120. When the first analysis result 112 is generated based on a plurality of preprocessing results, the processor 130 may generate a query for each of the plurality of preprocessing results and transmit the query to the visualization format database 120, and may generate the first visualization format 160 by combining visualization format information responses received from the visualization format database 120 or adding a priority. The processor 130 may transmit the first visualization format 160 to an external display device via the communication interface 140 and control the display device so that the first visualization format 160 is visualized on the screen of the display device.

The first artificial neural network 110 may be an artificial neural network that has received the information obtained in such a manner that a professional diagnosed a plurality of types of diseases for a single body part included in each of a plurality of training medical images and has learned the function of diagnosing the plurality of types of diseases included in each of the plurality of training medical images. In this case, the first artificial neural network 110 may be an artificial neural network that has learned a function capable of diagnosing a plurality of types of diseases in one neural network model.

The factor that determines the first visualization format 160 provided by the processor 130 is information included in the first medical image 150, and is information included in the first analysis result 112 based on the analysis and inference of the first artificial neural network 110. In addition, the first visualization format 160 based on the first analysis result 112 may be derived through cooperation between a clinical characteristic (disease code) or functional characteristic (segmentation, detection, identification, diagnosis, or measurement) included in the first analysis result 112 and the rules stored in the visualization format database 120.

An example of the first visualization format 160 based on the first analysis result 1120 will be described later in conjunction with FIGS. 7 to 14.

Figure 2:
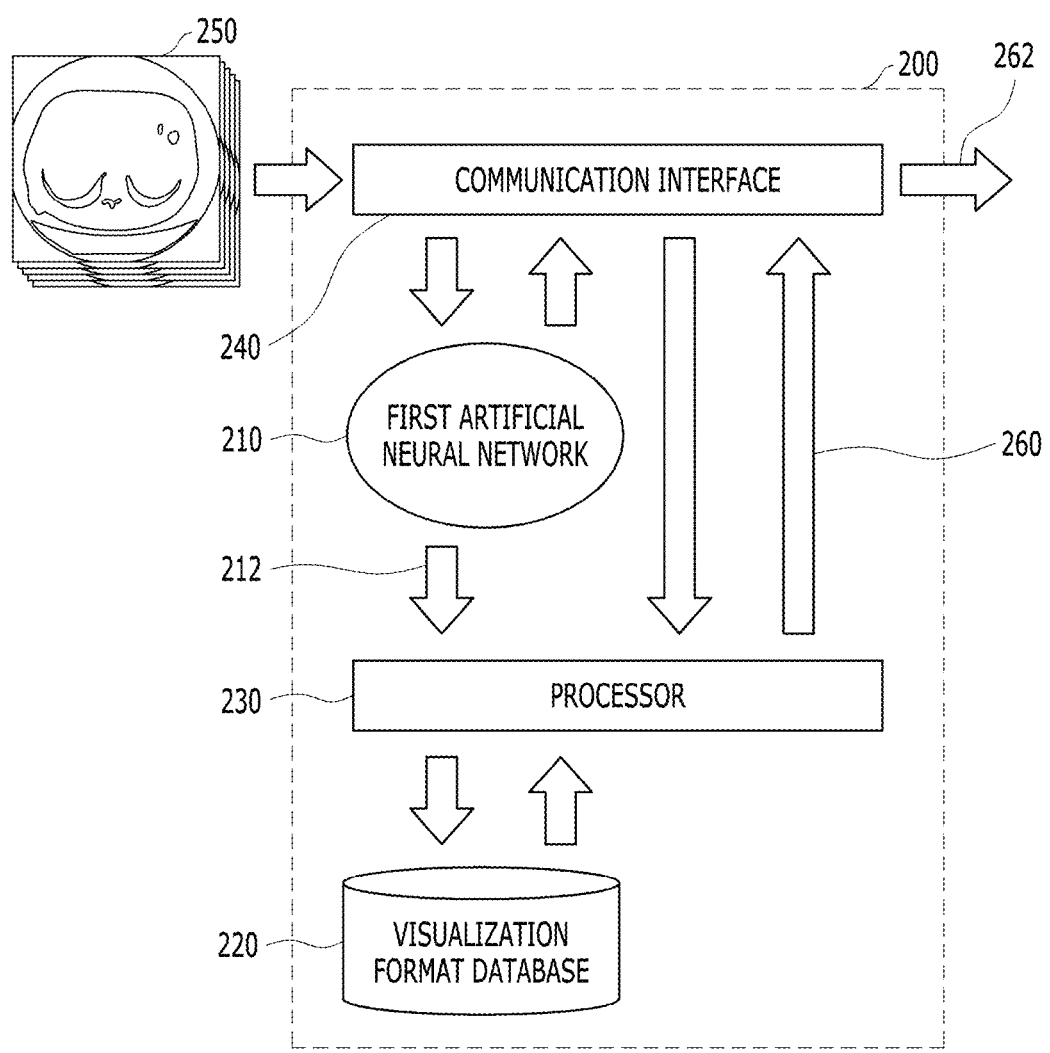
FIG. 2 is a diagram showing a medical image reading assistance apparatus that provides a representative image based on an analysis result of a medical artificial neural network according to an embodiment of the present invention.

FIG. 2 is a diagram showing a medical image reading assistance apparatus that provides a representative image based on an analysis result of a medical artificial neural network according to an embodiment of the present invention.

Referring to FIG. 2, the medical image reading assistance apparatus according to the present embodiment includes a computing system 200. The computing system 200 includes at least one processor 230. The computing system 200 may further include a visualization format database 220. The at least one processor 230 acquires or receives a first analysis result 212 obtained through the inference of a first artificial neural network 210 for a first medical image 250, generates a first visualization format 260, which is a representative visualization format of the first medical image 250, based on the first analysis result 212 in cooperation with the visualization format database 220, and generates visualization information 262 in which the first medical image 250 and the first analysis result 212 are displayed on a screen based on the first visualization format 260.

In FIG. 2, there is shown an embodiment in which the first artificial neural network 210 is included in the computing system 200. The communication interface 240 may acquire or receive the first medical image 250 from the outside. The communication interface 240 may transmit the first medical image 250 to the first artificial neural network 210 under the control of the processor 230, and may transmit the first medical image 250 to the processor 230.

The first artificial neural network 210 may generate the first analysis result 212 for the first medical image 250 under the control of the processor 230, and may transmit the first analysis result 212 to the processor 230 under the control of the processor 230.

The processor 230 may generate the first visualization format 260 based on the first analysis result 212 and the first medical image 250, and may transmit the first visualization format 260 to the communication interface 240.

Since the other operations of the processor 230, the communication interface 240, the first artificial neural network 210, and the visualization format database 220 are the same as those of the processor 130, the communication interface 140, the first artificial neural network 110, and the visualization format database 120, redundant descriptions thereof are omitted.

Figure 3:
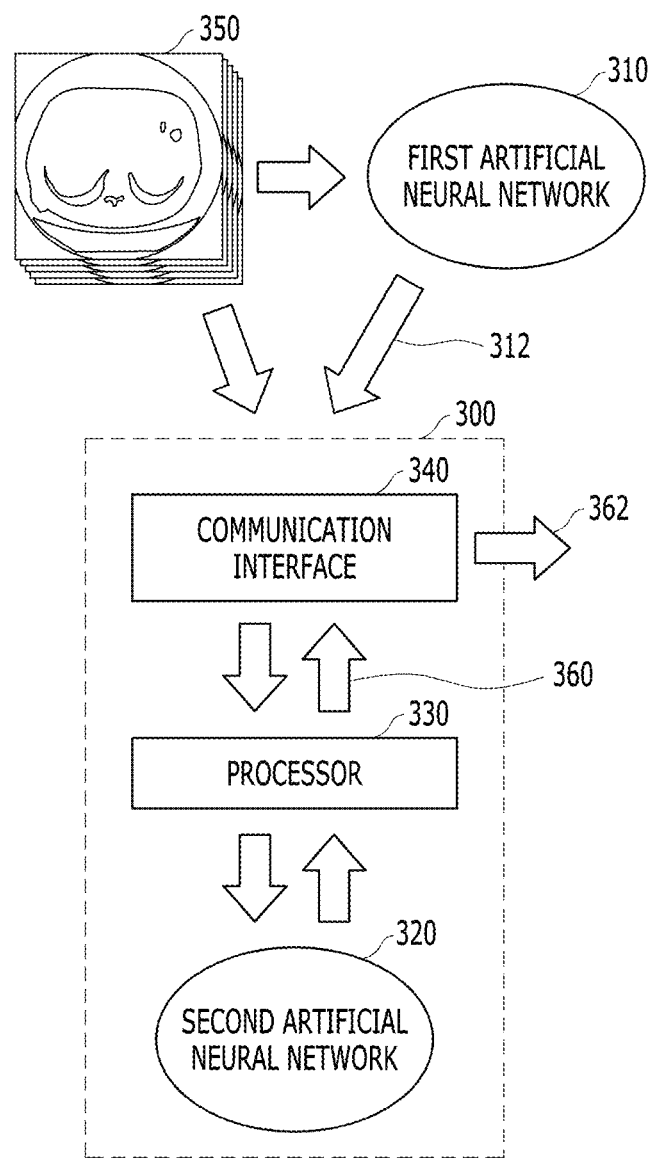
FIG. 3 is a diagram showing a medical image reading assistance apparatus that provides a representative image based on an analysis result of a medical artificial neural network according to an embodiment of the present invention.

FIG. 3 is a diagram showing a medical image reading assistance apparatus that provides a representative image based on an analysis result of a medical artificial neural network according to an embodiment of the present invention.

Referring to FIG. 3, the medical image reading assistance apparatus according to the present embodiment includes a computing system 300. The computing system 300 includes at least one processor 330.

In FIG. 3, there is shown an embodiment in which a second artificial neural network 320 is included. The computing system 300 may further include a second artificial neural network 320. The at least one processor 330 acquires or receives a first analysis result 312 obtained through the inference of the first artificial neural network 310 on the first medical image 350, generates a first visualization format 360, which is a representative visualization format of the first medical image 350, through the inference of the second artificial neural network 320 by providing the first analysis result 312 as an input of the second artificial neural network 320, and generates visualization information 362 in which the first medical image 350 and the first analysis result 312 are displayed on a screen.

The second artificial neural network 320 may be an artificial neural network that has received a plurality of second visualization formats selected by a professional for a plurality of third analysis results obtained for a plurality of second medical images, which are other training images, and has learned the function of generating visualization formats based on the relevance between the plurality of third analysis results and the plurality of second visualization formats. The at least one processor 330 may input the first analysis result 312 to the second artificial neural network 320, and may control the artificial neural network 320 to obtain the first visualization format 360 through the inference of the second artificial neural network 320. According to a modified embodiment of the present invention, the processor 330 may receive an output result obtained through the inference of the second artificial neural network 320, and may generate the first visualization 360 based on the output result obtained through the inference of the second artificial neural network 320. In this case, the processor 330 generates the first visualization format 360 based on the output result obtained through the inference of the second artificial neural network 320 and context information derived for the first medical image 350.

Since the other operations of the processor 330, the communication interface 340, and the first artificial neural network 310 are the same as the processor 130, the communication interface 140, and the first artificial neural network 110 of FIG. 1, redundant descriptions thereof are omitted.

Figure 4:
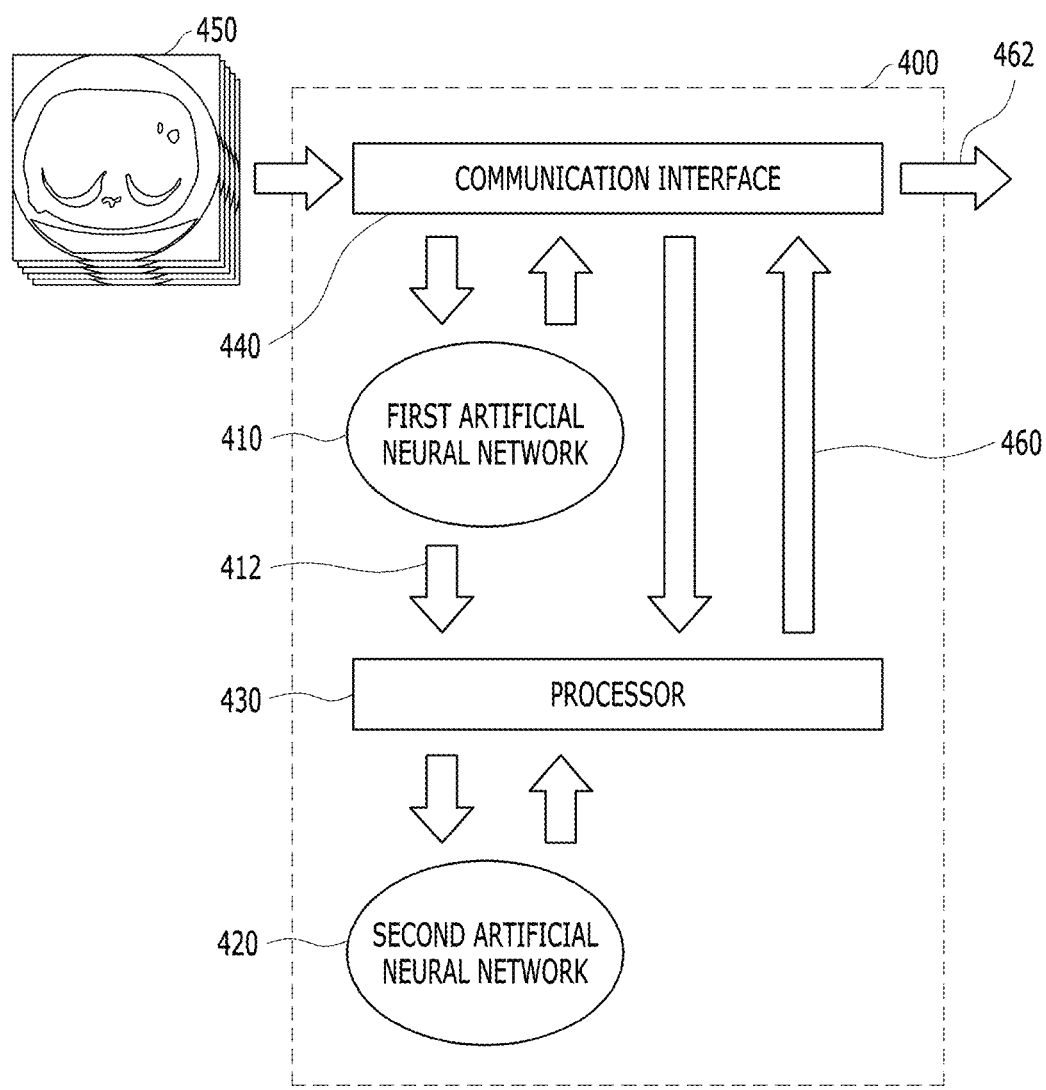
FIG. 4 is a diagram showing a medical image reading assistance apparatus that provides a representative image based on an analysis result of a medical artificial neural network according to an embodiment of the present invention.

FIG. 4 is a diagram showing a medical image reading assistance apparatus that provides a representative image based on an analysis result of a medical artificial neural network according to an embodiment of the present invention.

Referring to FIG. 4, the medical image reading assistance apparatus according to the present embodiment includes a computing system 400. The computing system 300 includes at least one processor 430.

In FIG. 4, there is shown an embodiment in which a first artificial neural network 410 and a second artificial neural network 420 are included in the computing system 400. The at least one processor 430 acquires or receives a first analysis result 412 obtained through the inference of the first artificial neural network 410 for the first medical image 450, generates a first visualization format 460, which is a representative visualization format of the first medical image 450, through the inference of the second artificial neural network 420 by providing the first analysis result 412 as an input of the second artificial neural network 420, and generates visualization information 462 in which the first medical image 450 and the first analysis result 412 are displayed on a screen based on the first visualization format 460.

Since the other operations of the processor 430, the communication interface 440, the first artificial neural network 410, and the second artificial neural network 420 are the same as those of the processor 330, the communication interface 340, and the first artificial neural network 310, and the second artificial neural network 320, redundant descriptions thereof are omitted.

Figure 5:
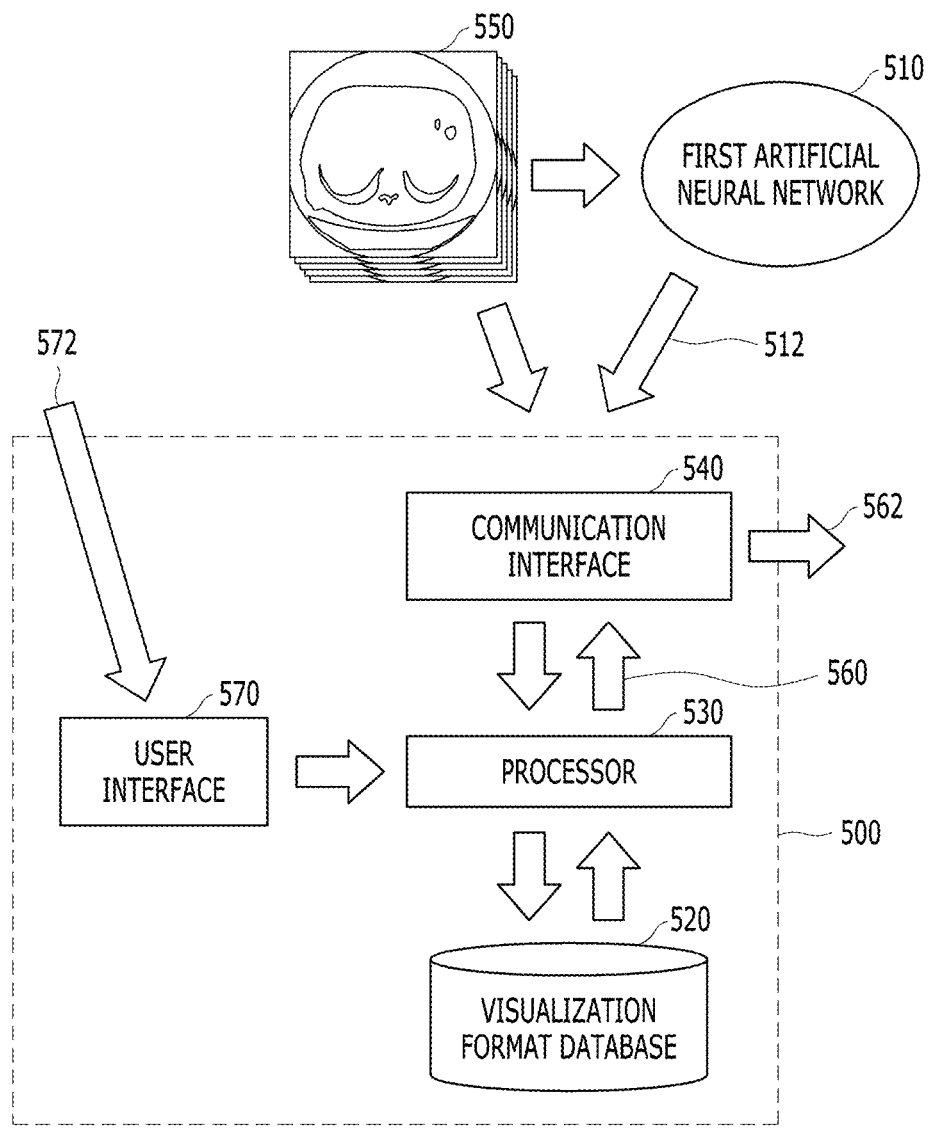
FIG. 5 is a diagram showing a medical image reading assistance apparatus that provides a representative image based on an analysis result of a medical artificial neural network according to an embodiment of the present invention.

FIG. 5 is a diagram showing a medical image reading assistance apparatus that provides a representative image based on an analysis result of a medical artificial neural network according to an embodiment of the present invention.

Referring to FIG. 5, the medical image reading assistance apparatus according to the present embodiment includes a computing system 500. The computing system 500 includes at least one processor 530. The computing system 500 may further include a visualization format database 520. The at least one processor 530 acquires or receives a first analysis result 512 obtained through the inference of the first artificial neural network 510 for the first medical image 550, generates a first visualization format 560, which is a representative visualization format of the first medical image 550, in cooperation with the visualization format database, and generates the visualization information 562 in which the first medical image 550 and the first analysis result 512 are displayed on a screen based on the first visualization format 560.

In FIG. 5, there is shown an embodiment in which the computing system 500 further includes a user interface 570 configured to receive a user input 572.

The at least one processor 530 may provide a first user menu adapted to receive information about a user's approval for the first analysis result 512 displayed on the screen based on the first visualization format 560, along with the visualization information 562, onto a display screen via the user interface 570. The first user menu may be a user menu that allows the user to select either "Confirm" or "Reject." According to another embodiment of the present invention, the first user menu may be provided as a visual, auditory, or tactile means, or a combination of two or more thereof.

The user interface 570 receives a user input 572, and transfers the user input 572 to the processor 530. The at least one processor 530 may interpret the user input 572, and, when the user does not approve the first analysis result 512, may provide a second user menu adapted to generate a second analysis result corresponding to the first analysis result 512 for the first medical image 550 independently from the first analysis result 512 onto a display screen or an additional user interface menu via the user interface 570 and/or the communication interface 540. The second user menu may be an interface menu that may generate a second analysis result that replaces the first analysis result 512. The second user menu may be an interface menu that may be partially automatically executed, that may be partially automatically executed, receive user input intermittently and interactively, generate the second analysis result, and replace the first analysis result 112 with the second analysis result. In addition, when the user does not approve the first analysis result 512, there may be provided a user menu that the user can independently generate a preprocessing result that is the basis for the generation of the first analysis result 112. The preprocessing result may also be generated manually or semi-automatically by the user menu.

Since the other operations of the processor 530, the communication interface 540, the first artificial neural network 510, and the visualization format database 520 are the same as the processor 130, the communication interface 140, the first artificial neural network 110, and the visualization format database 120, redundant descriptions thereof are omitted.

Figure 6:
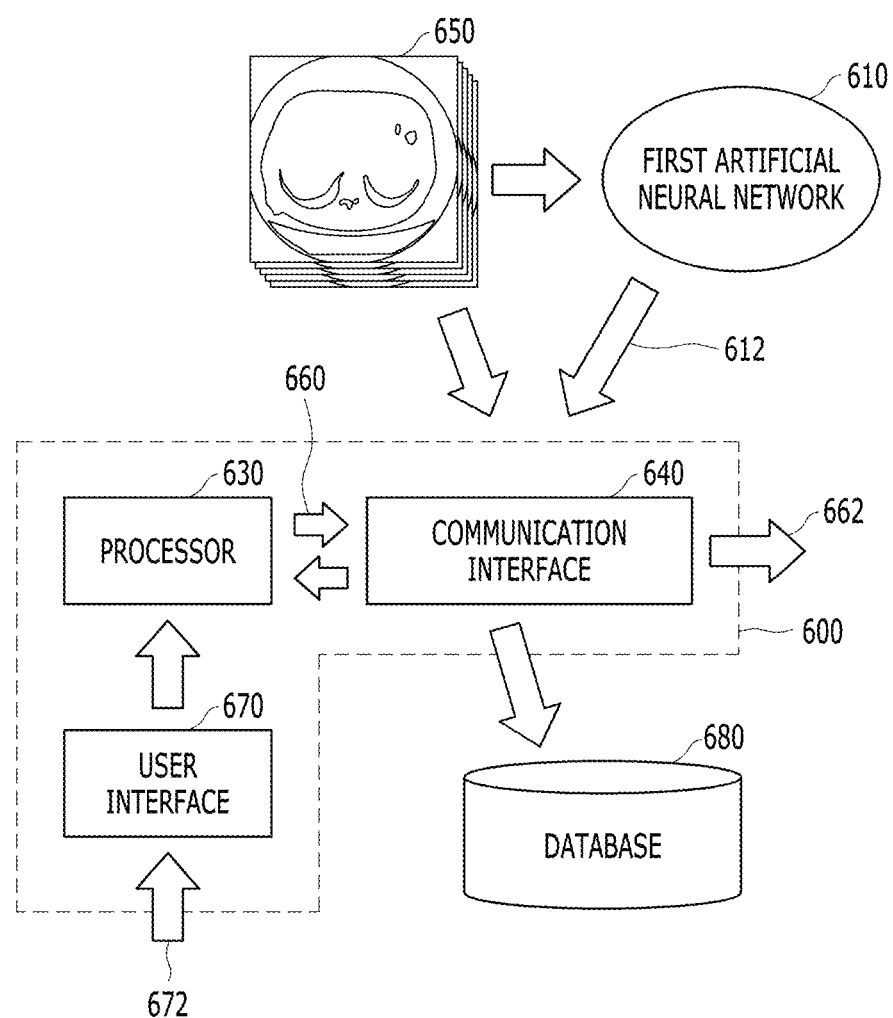
FIG. 6 is a diagram showing a medical image reading assistance apparatus that provides a representative image based on an analysis result of a medical artificial neural network according to an embodiment of the present invention.

FIG. 6 is a diagram showing a medical image reading assistance apparatus that provides a representative image based on an analysis result of a medical artificial neural network according to an embodiment of the present invention.

Referring to FIG. 6, the medical image reading assistance apparatus according to the present embodiment includes a computing system 600. The computing system 600 includes at least one processor 630. The at least one processor 630 acquires or receives a first analysis result 612 obtained through the inference of the first artificial neural network 610 for the first medical image 650 via a communication interface 640. The at least one processor 630 generates a first visualization format 660, which is a representative visualization format of the first medical image 650, based on the first analysis result 612, and may generate visualization information 662 in which the first medical image 650 and the first analysis result 612 are displayed on a screen based on the first visualization format 660. In this case, although not shown in FIG. 6, the at least one processor 630 may generate the first visualization format 660, which is a representative visualization format of the first medical image 650, based on the first analysis result 612, and may generate the visualization information 662, in which the first medical image 650 and the first analysis result 612 are displayed on the screen, based on the first visualization format 660 in cooperation with a visualization format database (not shown in FIG. 6).

As in the embodiment of FIG. 5, the at least one processor 630 of FIG. 6 may provide a first user menu adapted to receive information about a user's approval for the first analysis result 612 displayed on the screen based on the first visualization format 660, along with visualization information 662, onto the display screen via the user interface 670. The first user menu may be a user menu adapted to allow the user to select either "Confirm" or "Reject."

The user interface 670 may receive the user input 672, and transfers the user input 672 to the processor 630. The at least one processor 630 may interpret the user input 672, and, when the user approves the first analysis result 612, may store the first analysis result 612 in a database 680 in association with the first medical image 650.

In FIG. 6, there is shown an example in which the database 680 is located outside the computing system 600. The database 680 may be a picture archiving and communication system (PACS) database or a cloud-based database.

In the embodiment of FIG. 6, the computing system 600 may transmit and receive data via the external database 680 and the communication interface 640. The at least one processor 630 may store the first analysis result 612 in the database 680 in association with the first medical image 650 via the communication interface 640.

Since the other operations of the processor 630, the communication interface 640, the first artificial neural network 610, and the user interface 670 are the same as those of the processor 530, the communication interface 540, the first artificial neural network 510, and the user interface 570 of FIG. 5, redundant descriptions thereof are omitted.

Although an embodiment in which the database 680 is located outside the computing system 600 is shown in FIG. 6, it will be apparent to those skilled in the art that a database (not shown) may also be implemented to be located inside the computing system 600 according to another embodiment of the present invention.

In the embodiments of FIGS. 1 to 6, there are disclosed the medical image reading assistance apparatuses that improve medical image-based diagnosis and image analysis workflows in medical institutions and assist medical professionals in making image diagnosis.

As medical image analysis technology develops, image analysis algorithms based on artificial intelligence or artificial neural networks not only detect/diagnose specific lesions in images, but also obtain quantitative information about status of legion can be found in images on segmented regions (for example, organs and/or anatomical structures). The process of obtaining such quantitative information is sometimes called measurement. The results of the measurement may serve as information that assists medical professionals in reading images. No matter how accurate image analysis and/or image segmentation is, 100% accuracy cannot be achieved at the current technology level. Furthermore, in medical image analysis, even one failure can lead to a fatal consequence. Accordingly, it is considerably important to prepare for an alternative to the failure of image analysis.

If a measurement result is inaccurate or out of a reasonable range, it may be a case where image segmentation, which is a result of preprocessing process, fails or is inaccurate. Therefore, representative visualization formats can be derived related to visualization targets which is basis or pre-processed results that the measurement result depends on in the present invention.

For example, in a lung image, lung lobe segmentation and airway segmentation are important. Based on these segmentation results, quantitative information related to emphysema and airway wall thickness may be obtained using a medical image analysis algorithm or an artificial neural network.

In a cardiac image, the segmentation of blood vessels such as arteries/veins is important. Based on these segmentation results, quantitative information related to calcium scoring and the like may be obtained using a medical image analysis algorithm or an artificial neural network.

As to the result of the measurement process of acquiring quantitative information, when an image segmentation process, which is a preprocessing process, is not accurate or image segmentation fails, there may be cases where a measurement result exceeds a reasonable range, for example, a quantitative measurement result is excessively low or excessively high.

When the quantitative measurement result is excessively high above the upper limit of a reasonable range, there is a high possibility that a medical professional will check the medical image once more to correct the incorrect measurement. In contrast, a problem may arise when the quantitative measurement result is excessively low below the lower limit of a reasonable range. In this case, when a medical professional refers to only the analysis result of the medical image analysis algorithm or artificial neural network, there is a possibility that the actual disease will be overlooked without being discovered.

However, for the above-described reasons, it will be considerably burdensome for a medical professional to review all the original medical images once again in all cases where quantitative analysis results are provided, and it is completely consistent with the purpose of using the quantitative analysis results provided automatically. Accordingly, it would be an effective way to improve workflows and prevent errors to provide a quantitative analysis result and also provide a user interface that, in order to assist the determination of whether the quantitative analysis result is accurate or there is no error out of a reasonable range in the quantitative analysis result, visualizes a representative image together with the quantitative analysis result and allows a user, who is a medical professional, to check the quantitative analysis result visualized together with the representative image.

In this case, although the user may be a clinician or radiologist, who is a medical professional, the user may be an assistant staff member who has only knowledge of a sufficient level to check whether a basic preprocessing process such as image segmentation has been performed within a reasonable range depending on an object to be diagnosed. In other words, even when the user does not have clinical knowledge but has representativeness of a sufficient level to check whether the segmentation of a specific region in the image has been accurately performed, he or she may derive a representative visualization format of the present invention.

Furthermore, as shown in the embodiments of FIGS. 1 to 6, it is also important as a workflow to provide a user menu that provides assistance such that a correct analysis result can be measured by manually or semi-automatically re-analyzing the analysis result rejected by the user.

It is also important as a workflow to provide the configuration of storing the analysis result approved by the user in the PACS database so that it can be used for an original diagnosis purpose (for a diagnosis purpose in a medical institution).

Each of the first artificial neural networks 110, 210, 310, 410, 510, and 610 shown in the embodiments of FIGS. 1 to 6 may have an image analysis function related to a plurality of diseases or lesions. In this case, the first artificial neural network 110, 210, 310, 410, 510, or 610 may include a plurality of image analysis modules therein. Each of the visualization format databases 120, 220, and 520 or second artificial neural networks 320 and 420 of the present invention may have information about representative visualization formats for a plurality of image analysis modules, a plurality of diseases, a plurality of lesions, or a plurality of image analysis results. In this case, each of the computing systems 100, 200, 300, 400, 500, and 600 of the present invention may generate information about the type of a currently input analysis result and a lesion or disease to which the analysis result is related as context information, and may derive a representative visualization format optimized in response to the context information.

The factor that determines each of the representative visualization formats 160, 260, 360, 460, 560, and 660 comprises information related to the lesion, findings, and/or clinical information included in the first medical image 150, 250, 350, 450, 550, or 650, and further comprises information included in the first analysis result 112, 212, 312, 412, 512, or 612 generated by the analysis of the first artificial neural network 110, 210. 310, 410, 510, or 610, and further comprises information related to the basis or the pre-processed results that the first analysis result 112, 212, 312, 412, 512, or 612 depends on.

Furthermore, when the representative visualization format 160, 260, 360, 460, 560, or 660 for the first analysis result 112, 212, 312, 412, 512, 612 includes a plurality of reconstructed or reformatted images of a medical image, a screen layout in which the plurality of reconstructed or reformatted images are displayed may be included in the visualization information 162, 262, 362, 462, 562, or 662 in order to visualize them. In this case, the visualization information 162, 262, 362, 462, 562, or 662 may include some of the information defined by the hanging protocol. Meanwhile, since the visualization format information additionally includes information such as the type of reconstruction or reformatting defined in the hanging protocol, as well as the direction of a view derived based on the medical image and the analysis results, it may further include specific information than the information defined in the hanging protocol.

Figure 7:
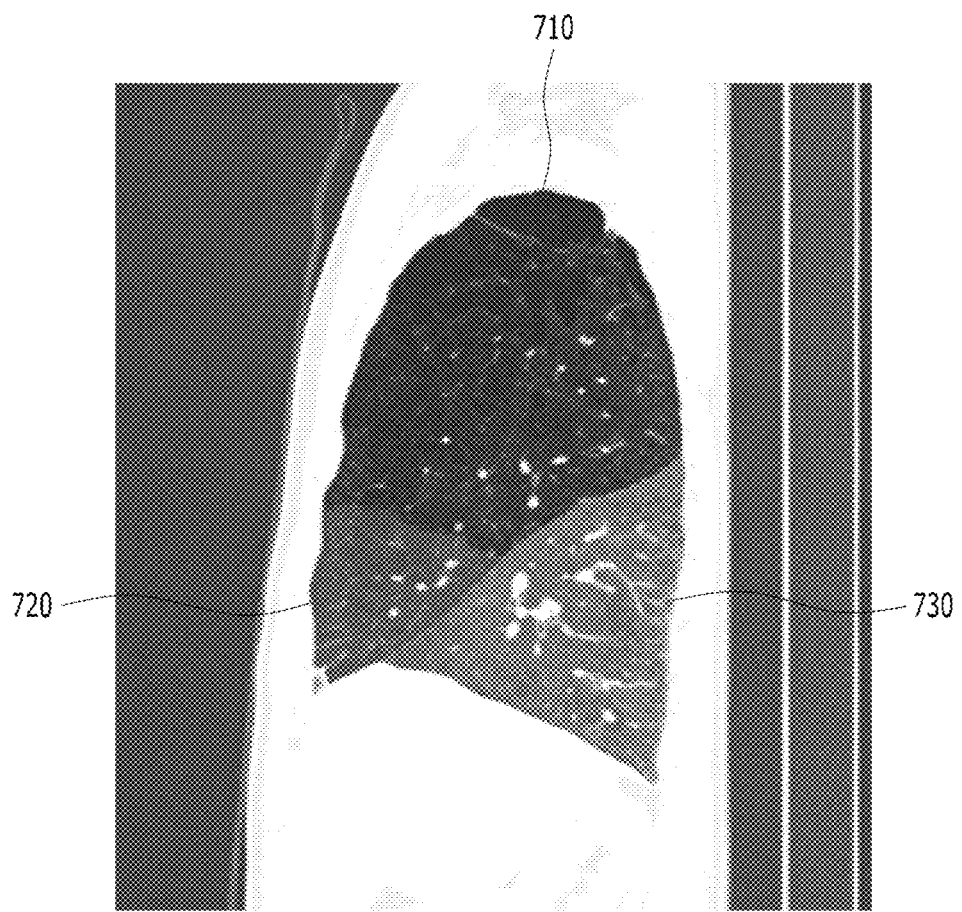
FIGS. 7 to 14 are diagrams showing examples in which a representative visualization format based on a first analysis result of a first artificial neural network is derived according to an embodiment of the present invention.

FIG. 7 is a diagram showing an example in which a representative visualization format based on a first analysis result of a first artificial neural network is derived according to an embodiment of the present invention.

Referring to FIG. 7, there is shown a sagittal image of the center portion of the left lung, which is derived as a representative visualization format based on the results of lung lobe segmentation and low attenuation area (LAA) analysis.

The sagittal image of the center portion of the left lung is shown together with the result in which the left lung has been segmented into three lung lobes 710, 720, and 730. In this case, the sagittal image of the center portion of the left lung is one of the representative visualization formats according to the analysis result, and the result of the segmentation of the left lung into the three lung lobes 710, 720, and 730 is overlaid and visualized on the sagittal image as a preprocessing result corresponding to or included in the image analysis result.

The LAA is a result of the analysis of a CT image including the lungs, and may mean an area in which a brightness value in the CT image is darker than a reference value. In normal alveoli, the brightness value thereof may change within a CT image depending on the breathing phase. However, an area that is continuously maintained at a brightness value smaller than a specific reference value in the CT image of the lungs is an image filled with air and is considered to have ruptured or inactivated alveoli, and thus the area may be determined to be an area not helpful to breathing.

The quantitative analysis result for the LAA may be expressed as the ratio of the volume of regions in which the brightness value is maintained below a reference value (e.g., −950 HU) within a specific area to the volume of the corresponding area. Another quantitative analysis result for the LAA may be expressed by a method of classifying the sizes of LAA regions and counting and displaying the number of LAA regions for each size. Such a quantification result varies depending on a patient's breathing level (how far the patient breathed). When it is processed using a log calculation, a constant value independent of the breathing level is obtained, and may be provided as an index for the patient's overall lung capacity. The quantitative measurement result for the LAA may be provided to a user for the diagnosis of chronic obstructive pulmonary disease (COPD) or the like, and may assists diagnosis.

The LAA analysis result is obtained through an image processing process including a plurality of steps.

The lung CT image may be segmented into the whole Lung, the left lung, and the right lung. The lung lobes of each of the left and right lungs may be segmented.

A reference area for deriving the ratio of LAA regions for each area in the LAA analysis result may be the segmented lung lobe or left/right lung.

If there is an error in the plurality of preprocessing steps required to derive the LAA analysis result, the reliability of the LAA analysis result may be lowered.

Accordingly, based on the analysis result, the preprocessing results of the plurality of preprocessing steps performed to reach the analysis result may be visualized together with a representative visualization format and provided together with the analysis result.

As described above, FIG. 7 shows an embodiment that may be provided to a user as one of the representative visualization formats for the LAA analysis result based on the LAA analysis result.

Figure 8:
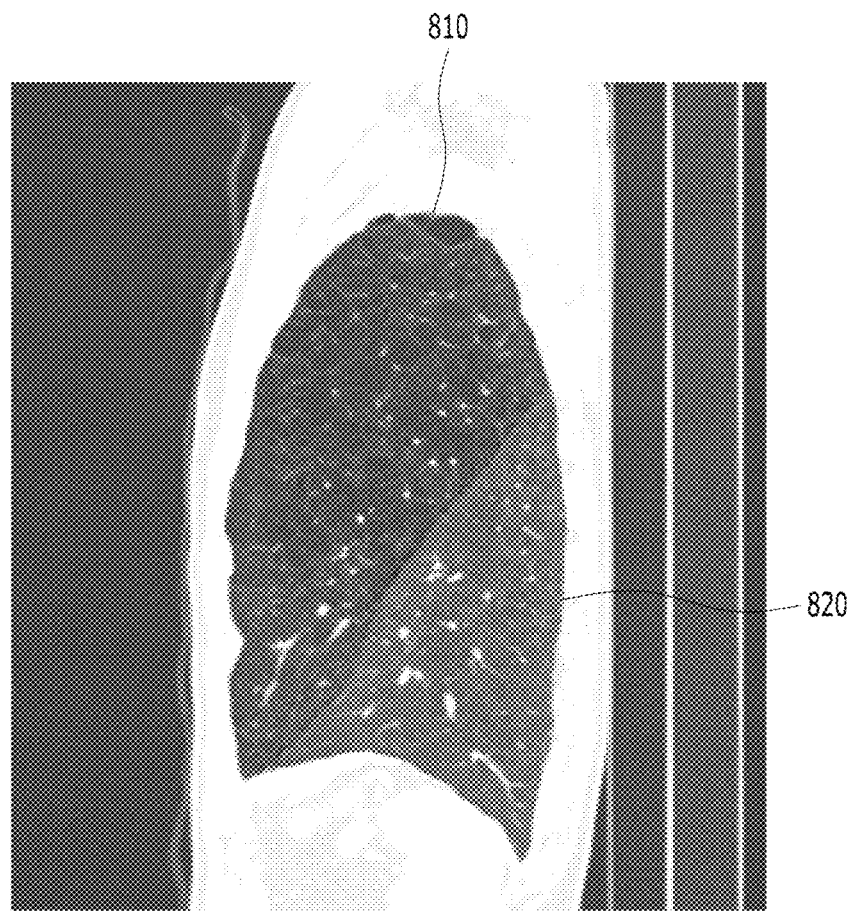

FIG. 8 is a diagram showing an example in which a representative visualization format is derived based on a first analysis result of a first artificial neural network according to an embodiment of the present invention.

FIG. 8 is a sagittal image of the center portion of the right lung in which there are shown two lung lobes 810 and 820 segmented from the right lung.

FIG. 8 shows the result of the preprocessing process performed to reach the LAA analysis result, which may be provided to a user as one of the representative visualization formats derived based on the LAA analysis result.

Figure 9:
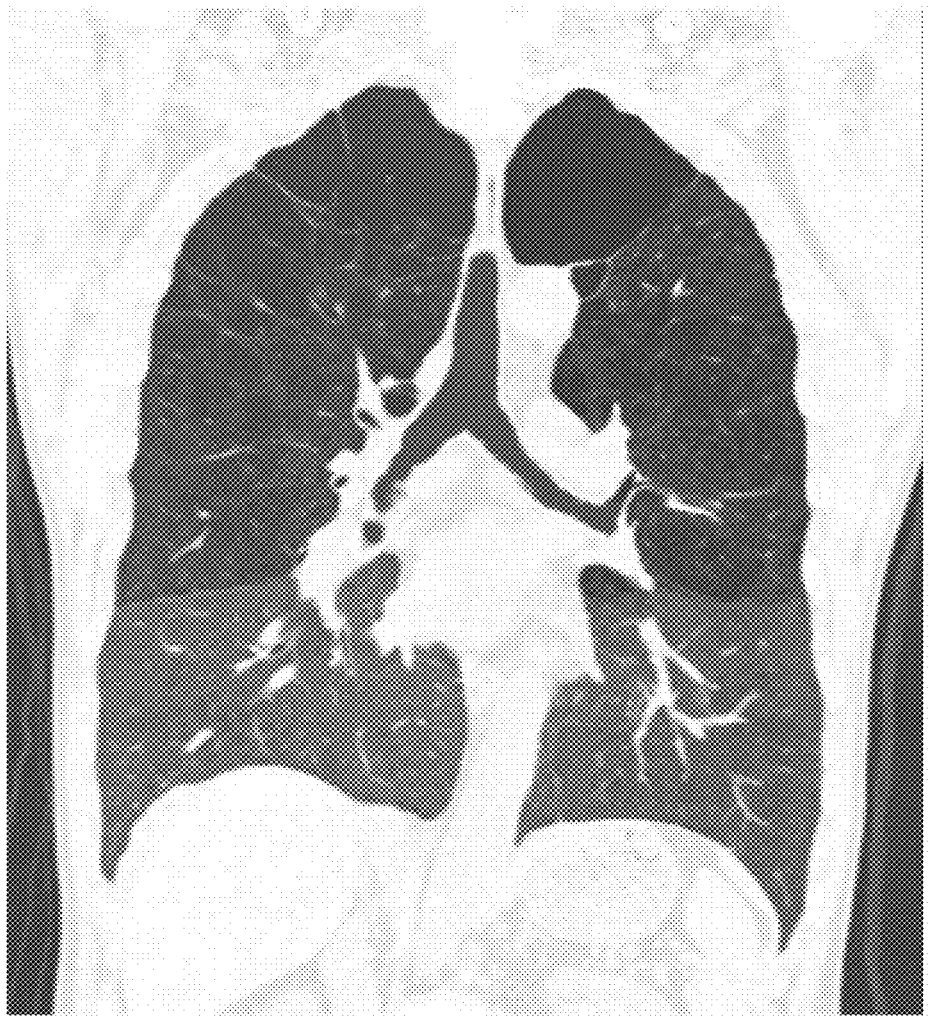

FIG. 9 is a diagram showing an example in which a representative visualization format is derived based on a first analysis result of a first artificial neural network according to an embodiment of the present invention.

FIG. 9 is a coronal image of tracheal branches, which may be provided to a user as one of the representative visualization formats effective for a user to evaluate the result of lung lobe segmentation. According to an embodiment of the present invention, instead of FIGS. 7 and 8, FIG. 9 may be provided to the user together with an LAA analysis result. According to another embodiment, all of FIGS. 7 to 9 may be provided to the user together. FIG. 9 may be a visualization format that assists a user in effectively evaluating the result of lung lobe segmentation by representatively visualizing an area where image segmentation is likely to fail rather than showing the overall image segmentation result.

Figure 10:
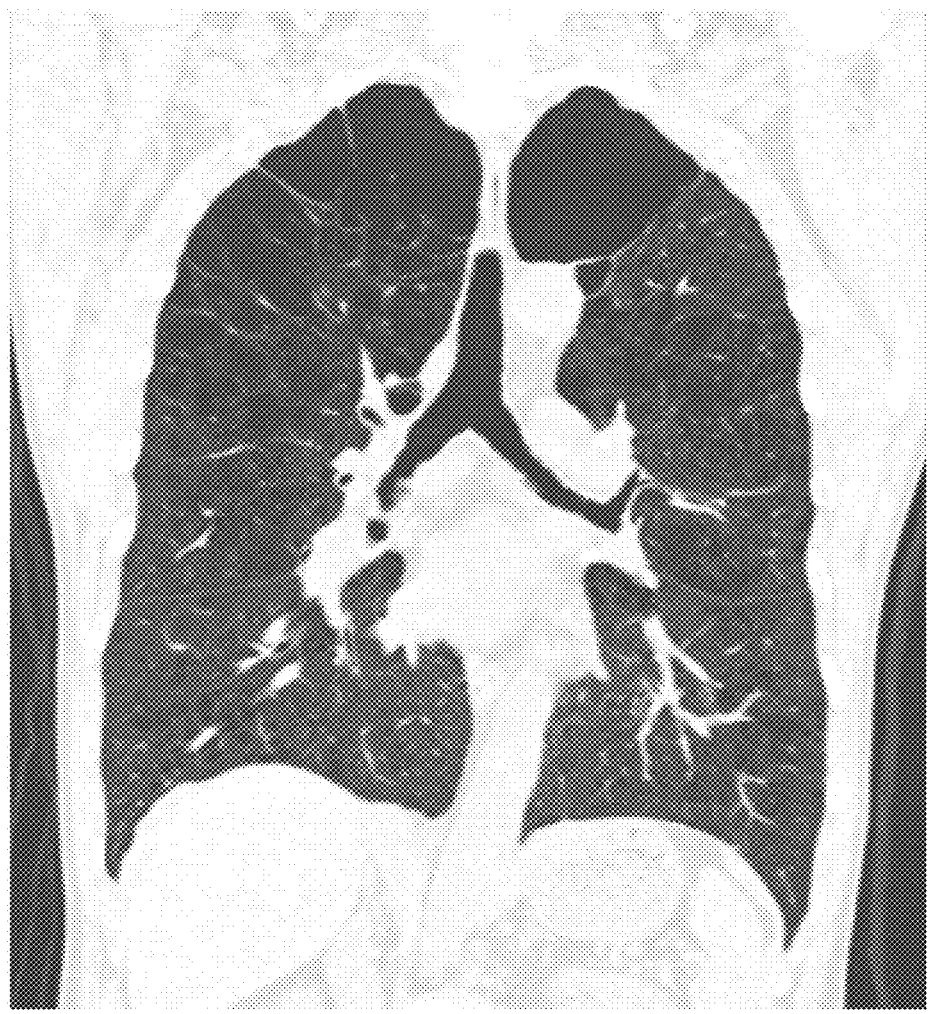

FIG. 10 is a diagram showing an example in which a representative visualization format is derived based on a first analysis result of a first artificial neural network according to an embodiment of the present invention.

FIG. 10 is one of the representative visualization formats for displaying detected LAA areas on a coronal image of tracheal branches.

Figure 11:
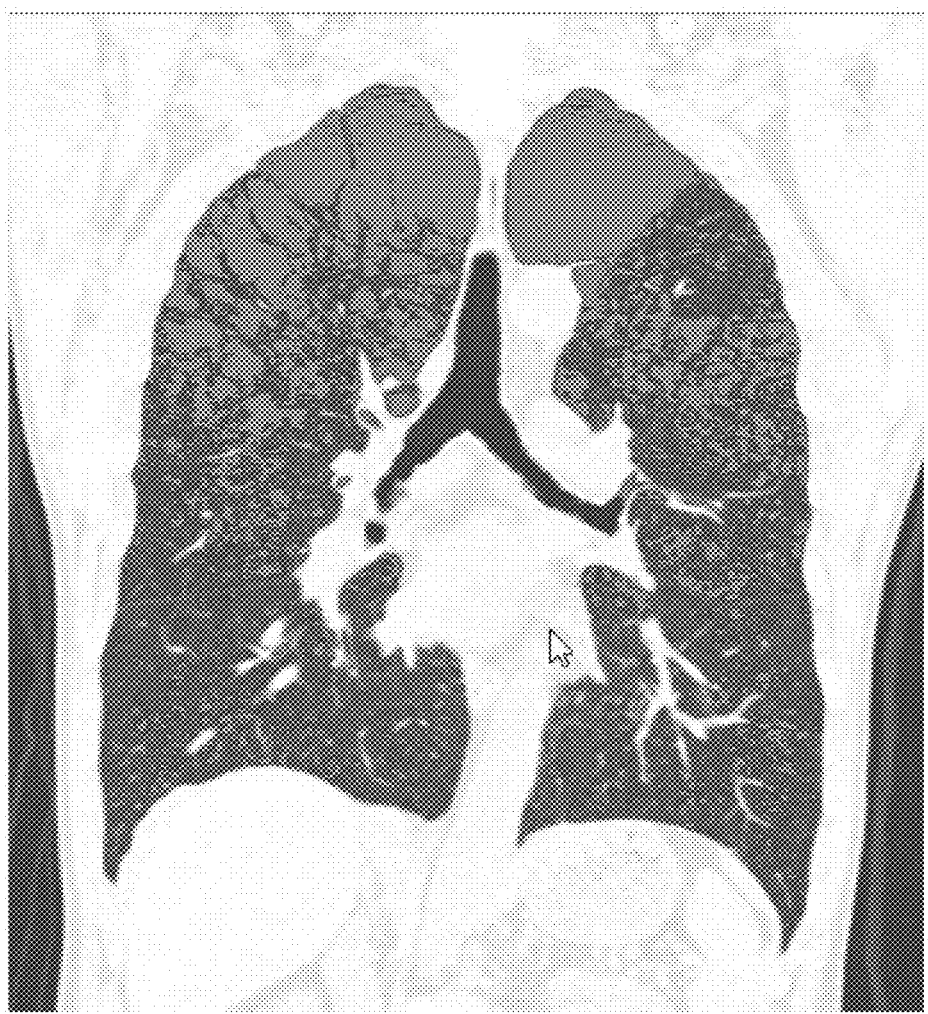

FIG. 11 is a diagram showing an example in which a representative visualization format based on a first analysis result of a first artificial neural network is derived according to an embodiment of the present invention.

FIG. 11 shows an example in which detected LAA regions, which is an analysis result, are visualized by overlaying the detected LAA regions on the representative visualization image of FIG. 10. When the image of FIG. 11 is displayed together with the analysis result for calculating the ratio of the LAA regions in a specific area, the medical image reading assistance apparatus of the present invention may assist the user in determining whether the ratio between the left lung/right lung and the portions to be segmented into the lung lobes in the left lung/right lung and the LAA regions in FIG. 11 has been reasonably calculated.

Although not shown in FIG. 11, detected LAA regions may be visualized using visualization elements (color, pattern, and/or brightness) classified based on the sizes of the LAA regions according to another embodiment of the present invention.

Figure 12:
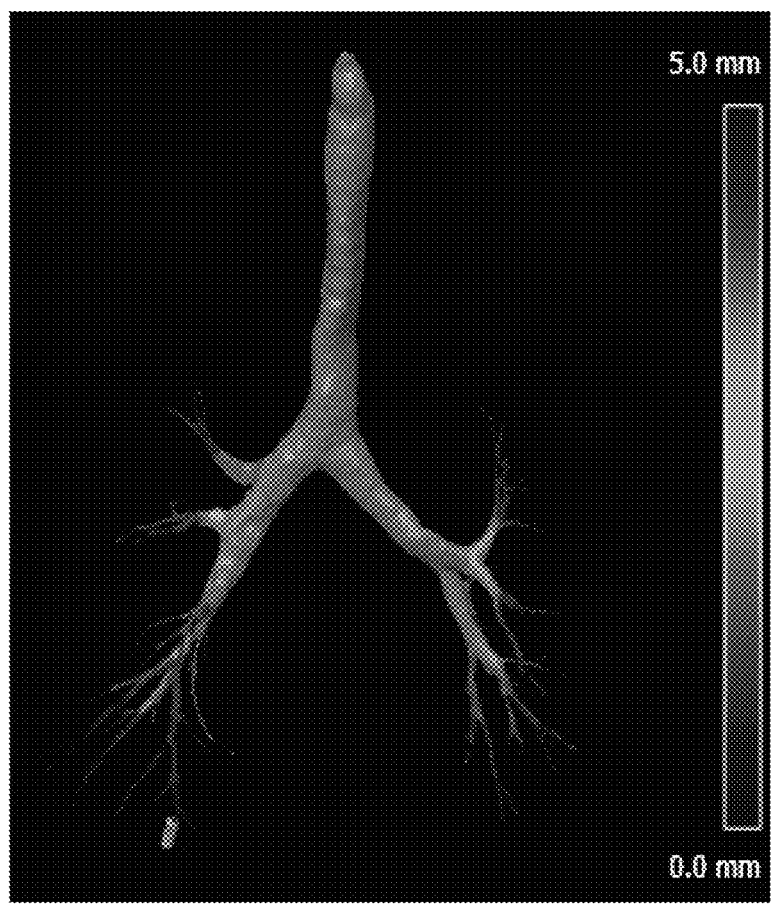

FIG. 12 is a diagram showing an example in which a representative visualization format based on a first analysis result of a first artificial neural network is derived according to an embodiment of the present invention.

When the analysis result is related to airway segmentation and quantification based on airway segmentation such as airway wall thickness measurements, the airway segmentation may be both an analysis result and a preprocessing result. In this case, a representative visualization format may be generated such that the analysis result and the preprocessing result are included in the representative visualization format together. In FIG. 12, the airway segmentation result of each of the first medical images 150, 250, 350, 450, 550, and 650, which is a preprocessing result, may be represented as a 3D volume rendering image in a frontal direction of lungs, a visualization element such as color, brightness, saturation, and/or pattern may be added to the 3D volume rendering image, and a quantification result, which is the first analysis result 112, 212, 312, 412, 512, or 612, may be visualized together with the 3D volume rendering image of the first medical image 150, 250, 350, 450, 550, or 650. In this case, each of the first visualization format 160, 260, 360, 460, 560, and 660 may include the 3D volume rendering image of the first medical image 150, 250, 350, 450, 550, or 650 and the visualization element added thereto. In this case, the first visualization format 160, 260, 360, 460, 560, or 660 may be derived as a representative visualization format that can visualize the information of the first medical image 150, 250, 350, 450, 550, or 650, the preprocessing result, and the first analysis result 112, 212, 312, 412, 512, or 612 together.

In FIG. 12, airway wall thickness measurement analysis values are visualized and displayed together with an airway segmentation result. In this case, the quantitative airway wall thickness information may be visualized and identified with color.

A user may determine whether the airway segmentation result is accurate because the user can view the airway segmentation result together with the quantitative analysis result, and the user may receive basis information on whether the quantitative analysis result can be accepted as it is. The user's medical image reading process may be assisted by the medical image reading assistance apparatus of the present invention based on the image of FIG. 12 that is provided as a representative visualization format.

It is known that thickening of the airway wall can make it difficult for a patient to breathe. In general, it is known that the thickness of both the airway lumen and the airway wall is large on the trachea side and the thickness of the airway lumen and the airway wall is smaller toward the microbronchi side. In FIG. 12, a quantification result and a representative visualization format are shown such that the user can determine whether the thickness of the airway wall is appropriately quantified when the relative position thereof in the airway is taken into consideration.

Figure 13:
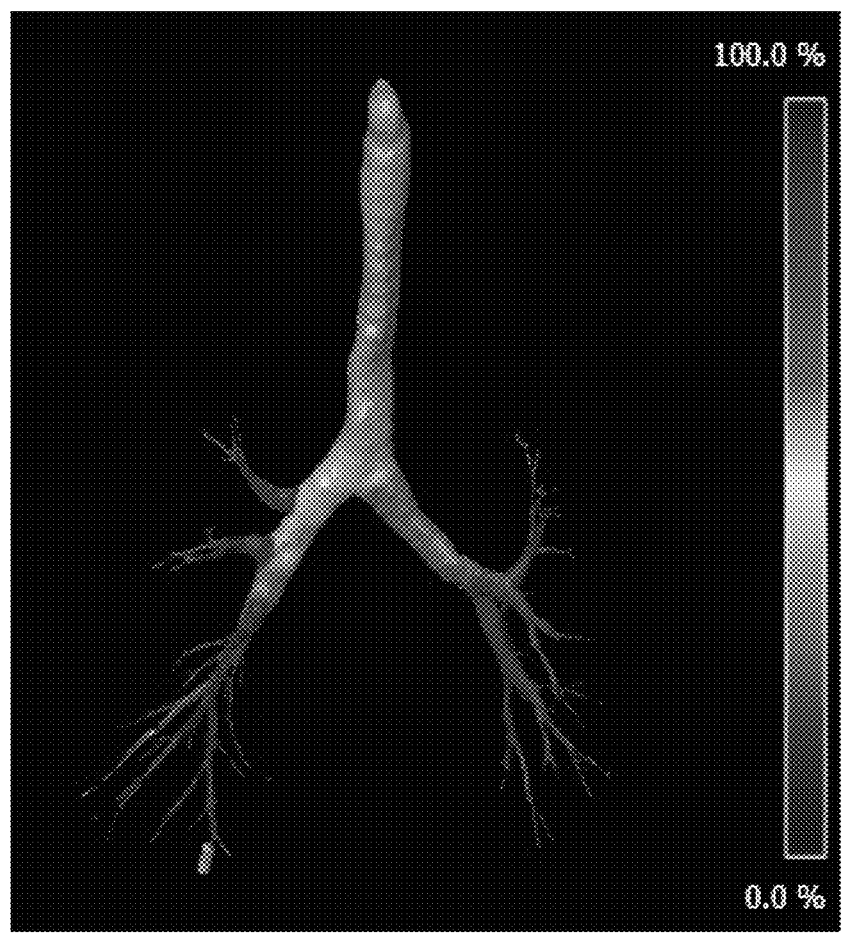

FIG. 13 is a diagram showing an example in which a representative visualization format based on a first analysis result of a first artificial neural network is derived according to an embodiment of the present invention.

In FIG. 13, the airway segmentation result and airway wall area % measurement analysis values are visualized and displayed together. In this case, the quantitative airway wall area % information may be visualized and identified with color.

As in FIG. 12, a user may determine whether the airway segmentation result is correct because he or she can view the airway segmentation result together with the quantification analysis result, and may receive basis information about whether the quantitative analysis result can be accepted as it is. The user's medical image reading process may be assisted by the medical image reading assistance apparatus of the present invention based on the image of FIG. 13 that is provided as a representative visualization format.

In FIG. 13, the quantification result and the representative visualization format are shown such that the user can determine whether the airway wall area % is appropriately quantified by taking into consideration the relative position thereof in the airway. In addition, for an area where the airway wall area % information thereof is 100% or close to 100%, when the user is a clinician or a radiologist, he or she may diagnose a patient's disease by taking into consideration the analysis result and the representative visualization format visualized in FIG. 13.

Figure 14:
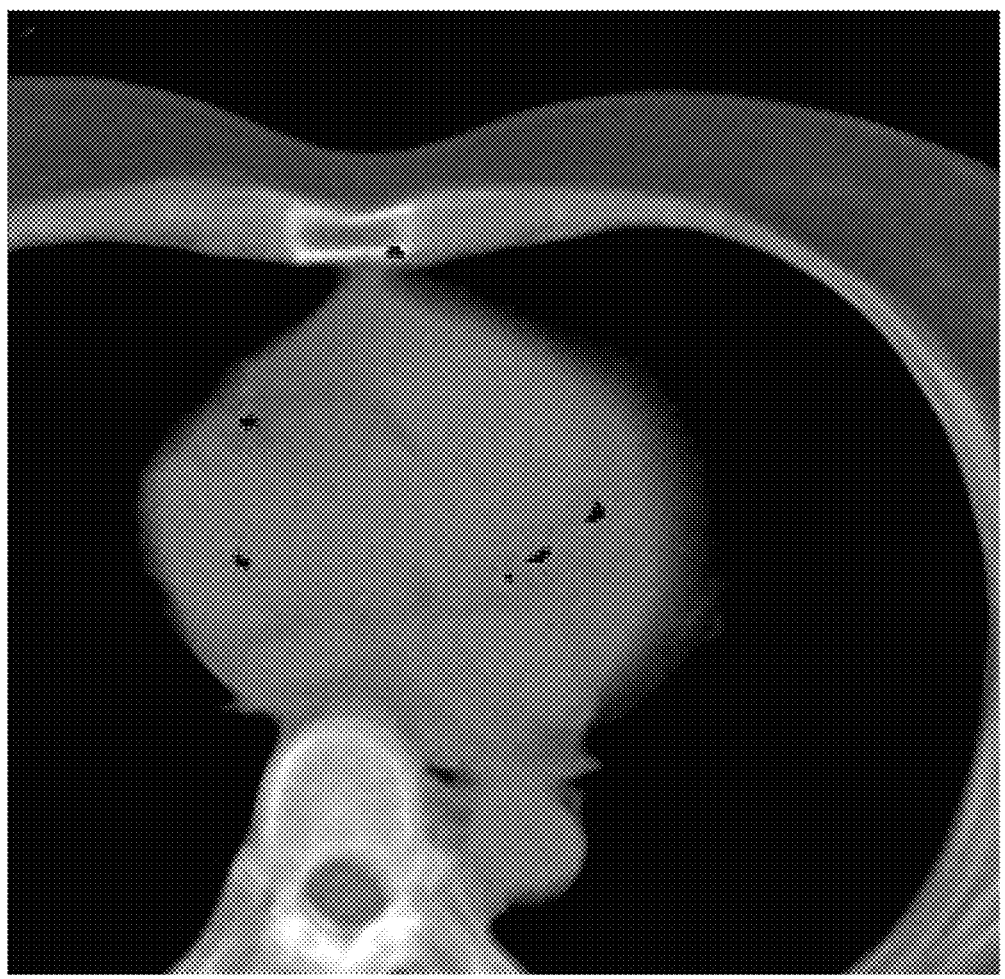

FIG. 14 is a diagram showing an example in which a representative visualization format based on a first analysis result of a first artificial neural network is derived according to an embodiment of the present invention.

FIG. 14 shows an example of a typical visualization format showing the results of the analysis/measurement of coronary artery calcification (CAC).

When an analysis result is the result of CAC, a cardiovascular segmentation process is performed as a preprocessing process. In this case, when there is an error in the cardiovascular segmentation process and a rib region is incorporated into a blood vessel region, an error in which a CAC measurement value is measured to be much larger than an actual value may occur.

When an analysis result is the result of CAC, a representative visualization format may be provided as an image that allows a user to determine that a bone region on a chest side is incorporated into a blood vessel segmentation region and classified as calcification. For example, one image in which all detected calcification regions are displayed on an axial image in which the slice thickness of a CT image is set to 50 mm may be generated as a representative visualization format and visualization information of an analysis result. In this case, the axial image of a CT image (or MIP image viewed in a direction from a head) is a representative visualization format, and all the detected calcification regions are overlaid on the representative visualization format to generate visualization information.

Figure 15:
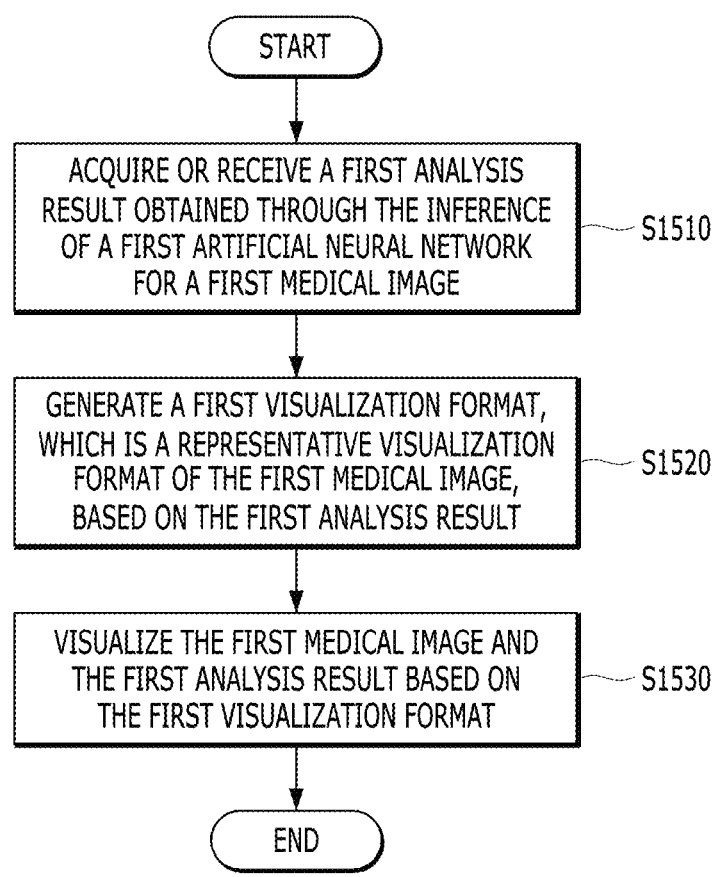
FIG. 15 is an operation flowchart showing an artificial neural network-based medical image reading assistance method according to an embodiment of the present invention.

FIG. 15 is an operation flowchart showing an artificial neural network-based medical image reading assistance method according to an embodiment of the present invention.

Referring to FIG. 15 and FIGS. 1 to 6 together, the artificial neural network-based medical image reading assistance method according to the present embodiment is performed by each of the computing systems 100, 200, 300, 400, 500, and 600. The computing system 100, 200, 300, 400, 500, or 600 includes the at least one processor 130, 230, 330, 430, 530, or 630. The method of the present invention includes: step S1510 of acquiring or receiving, by the at least one processor 130, 230, 330, 430, 530, or 630, the first analysis result 112, 212, 312, 412, 512, or 612 through the inference of the first artificial neural network 110, 210, 310, 410, 510, or 610 for the first medical image 150, 250, 350, 450, 550, or 650; step S1520 of generating, by the at least one processor 130, 230, 330, 430, 530, or 630, the first visualization format 160, 260, 360, 460, 560, or 660, which is a representative visualization format of the first medical image 150, 250, 350, 450, 550, or 650, based on the first analysis result 112, 212, 312, 412, 512, or 612; and step S1530 of visualizing, by the at least one processor 130, 230, 330, 430, 530, or 630, the first medical image 150, 250, 350, 450, 550, or 650 and the first analysis result 112, 212, 312, 412, 512, or 612 based on the first visualization format 160, 260, 360, 460, 560, or 660 so that the first medical image 150, 250, 350, 450, 550, or 650 and the first analysis result 112, 212, 312, 412, 512, or 612 are displayed on a screen.

At step S1530 of visualizing the first medical image 150, 250, 350, 450, 550, or 650 and the first analysis result 112, 212, 312, 412, 512, or 612 based on the first visualization format 160, 260, 360, 460, 560, or 660, the at least one processor 130, 230, 330, 430, 530, or 630 may visualize the first medical image 150, 250, 350, 450, 550, or 650 and the first analysis result 112, 212, 312, 412, 512, or 612 based on the first visualization format 160, 260, 360, 460, 560, or 660 so that a first user menu adapted to receive information about a user's approval for the first analysis result 112, 212, 312, 412, 512, or 612 displayed on the screen based on the first visualization format 160, 260, 360, 460, 560, or 660 is included.

There may be further included the step of, if the user does not approve the first analysis result 112, 212, 312, 412, 512, or 612, providing, by the at least one processor 130, 230, 330, 430, 530, or 630, a second user menu adapted to generate a second analysis result capable of replacing the first analysis result 112, 212, 312, 412, 512, or 612 for the first medical image 150, 250, 350, 450, 550, or 650 independently of the first analysis result 112, 212, 312, 412, 512, or 612.

The second user menu may be a user menu that can manually or semi-automatically generate the second analysis result.

At step S1520 of generating the first visualization format 160, 260, 360, 460, 560, or 660, the at least one processor 130, 230, 330, 430, 530, or 630 may generate the first visualization format 160, 260, 360, 460, 560, or 660 based on at least one of image segmentation for the first medical image 150, 250, 350, 450, 550, or 650 included in the first analysis result 112, 212, 312, 412, 512, or 612, clinical diagnosis, and the result of the quantitative measurement of a segmented object within the first medical image 150, 250, 350, 450, 550, or 650.

The first visualization format 160, 260, 360, 460, 560, or 660 may include at least one of at least one view of the first medical image 150, 250, 350, 450, 550, or 650 related to the first analysis result 112, 212, 312, 412, 512, or 612, at least part of the first medical image 150, 250, 350, 450, 550, or 650 selected from the first medical image 150, 250, 350, 450, 550, or 650 based on the relevance to the first analysis result 112, 212, 312, 412, 512, or 612, and the reconstruction of the first medical image 150, 250, 350, 450, 550, or 650. The first analysis result 112, 212, 312, 412, 512, or 612 may be visualized together with the first visualization format 160, 260, 360, 460, 560, or 660 so that it can be classified based on quantitative information included in the first analysis result 112, 212, 312, 412, 512, and 612.

Referring to FIG. 15, and FIGS. 3 and 4 together, the computing system 300 or 400 may include the second artificial neural network 320 or 420 that is an artificial neural network that has received a plurality of second visualization formats selected by a professional for a plurality of third analysis results obtained for a plurality of second medical images and has learned the function of generating visualization formats based on the relevance between the plurality of third analysis results and the plurality of second visualization formats. In this case, at step S1520 of generating the first visualization format 360 or 460 based on the first analysis result 312 or 412, the at least one processor 330 or 430 may input the first analysis result 312 or 412 to the second artificial neural network 320 or 420, and may control the second artificial neural network 320 or 420 so that the first visualization format 360 or 460 is obtained through the inference of the second artificial neural network 320 or 420.

Referring to FIG. 15 and FIGS. 1, 3, 5, and 6 together, at step S1510 of acquiring or receiving, by the at least one processor 130, 330, 530, or 630, the first analysis result 112, 312, 512, or 612 obtained through the inference of the first artificial neural network 110, 310, 510, or 610 for the first medical image 150, 350, 550, or 650, the at least one processor 130, 330, 530, or 630 may acquire or receive the first analysis result 112, 312, 512, or 612 via the communication interface 140, 340, 540, or 640 that transmits and receives data to and from the first artificial neural network 110, 310, 510, or 610 outside the computing system 100, 300, 500, or 600.

Referring to FIG. 15 and FIG. 6 together, there may be further included the step of, when the user approves the first analysis result 612, storing, by the at least one processor 630, the first analysis result 612 in the database 680 in association with the first medical image 650.

In this case, the at least one processor 630 may store the first analysis result 612 in the database 680 in association with the first medical image 650 via the communication 640 through which the at least one processor 630 transmits and receives data to and from the database 680 outside the computing system 600.

The method according to an embodiment of the present invention may be implemented in the form of program instructions, and may be then recorded in a computer-readable storage medium. The computer-readable storage medium may include program instructions, data files, and data structures solely or in combination. Program instructions recorded on the storage medium may have been specially designed and configured for the present invention, or may be known to or available to those who have ordinary knowledge in the field of computer software. Examples of the computer-readable storage medium include all types of hardware devices specially configured to record and execute program instructions, such as magnetic media, such as a hard disk, a floppy disk, and magnetic tape, optical media, such as compact disk (CD)-read only memory (ROM) and a digital versatile disk (DVD), magneto-optical media, such as a floptical disk, ROM, random access memory (RAM), and flash memory. Examples of the program instructions include machine code, such as code created by a compiler, and high-level language code executable by a computer using an interpreter. These hardware devices may be configured to operate as one or more software modules in order to perform the operation of the present invention, and the vice versa.

However, the present invention is not limited to the embodiments. Like reference symbols in the drawings designate like components. The lengths, heights, sizes, widths, etc. introduced in the embodiments and drawings of the present invention may be exaggerated to help to understand.

According to the present invention, there may be provided a representative visualization format appropriate designed for a clinician or radiologist to judge an artificial intelligent-based image analysis result or make a decision on the analysis result within a workflow for the clinician or radiologist.

According to the present invention, reading time may be shortened and also the efficiency of a workflow may be increased such that a clinician or radiologist can spend time only for the work that is directly related to reading based on analysis results based on medical images in an environment equipped with artificial intelligence capable of performing the analysis of a number of functions on medical images.

According to the present invention, there may be provided a user interface and display environment that improve the efficiency of reading, assist a clinician or radiologist in deriving a more accurate diagnosis result within a short period time, and increase the accuracy of analysis.

According to the present invention, there may be provided a representative visualization format that facilitates clinical judgment and decision-making for the results of the artificial intelligence-based analysis and quantification of medical images.

According to the present invention, the results of the artificial intelligence-based analysis and quantification of medical images may be visualized and also preprocessing results obtained to provide the analysis result and the quantification result in terms of a workflow may be visualized, thereby assisting a medical professional in performing clinical judgment and decision-making.

According to the present invention, when a medical professional rejects artificial intelligence-based analysis and quantification results, the medical professional may be allowed to reject preprocessing results that are the basis for the derivation of the artificial intelligence-based analysis and quantification results, and also there may be provided a user menu that allows a preprocessing process, an analysis process, and a quantification process to be performed again independently of artificial intelligence.

Although the present invention has been described with reference to specific details such as the specific components, and the limited embodiments and drawings, these are provided merely to help a general understanding of the present invention, and the present invention is not limited thereto. Furthermore, those having ordinary skill in the technical field to which the present invention pertains may make various modifications and variations from the above detailed description.

Therefore, the spirit of the present invention should not be defined based only on the described embodiments, and not only the attached claims but also all equivalent to the claims should be construed as falling within the scope of the spirit of the present invention.

What is claimed is:

1. A medical image reading assistance apparatus for assisting reading of a medical image based on a medical artificial neural network, the medical image reading assistance apparatus comprising a computing system, wherein the computing system comprises at least one processor,
wherein the at least one processor is configured to:
acquire or receive a first analysis result obtained through inference of a first artificial neural network for a first medical image;
generate a first visualization format, which is a representative visualization format of the first medical image, based on the first analysis result; and
visualize the first medical image based on the first visualization format,
wherein the computing system further comprises a second artificial neural network formed as an artificial neural network that has received a plurality of second visualization formats selected by a professional for a plurality of third analysis results obtained for a plurality of second medical images and has learned a function of generating visualization formats based on relevance between the plurality of third analysis results and the plurality of second visualization formats, and wherein the at least one processor is further configured to input the first analysis result to the second artificial neural network and control the second artificial neural network so that the first visualization format is acquired through inference of the second artificial neural network.

2. The medical image reading assistance apparatus of claim 1, wherein the at least one processor is further configured to provide a first user menu adapted to receive information about a user's approval for the first analysis result visualized based on the first visualization format.

3. The medical image reading assistance apparatus of claim 2, wherein the at least one processor is further configured to, when the user does not approve the first analysis result, provide a second user menu adapted to generate a second analysis result corresponding to the first analysis result for the first medical image independently of the first analysis result.

4. The medical image reading assistance apparatus of claim 2, wherein the at least one processor is further configured to, when the user approves the first analysis result, store the first analysis result in a database in association with the first medical image.

5. The medical image reading assistance apparatus of claim 4, wherein the computing system further comprises a communication interface configured to transmit and receive data to and from the database disposed outside the computing system, and
wherein the at least one processor is further configured to store the first analysis result in the database in association with the first medical image via the communication interface.

6. The medical image reading assistance apparatus of claim 1, wherein the at least one processor is further configured to visualize the first analysis result by overlaying the first analysis result on the first visualization format of the first medical image.

7. The medical image reading assistance apparatus of claim 1, wherein the at least one processor is further configured to generate the first visualization format based on the first medical image and the first analysis result so that the first analysis result is included in the first visualization format.

8. The medical image reading assistance apparatus of claim 1, wherein the first visualization format comprises at least one of at least one view of the first medical image, at least part of the first medical image selected from the first medical image based on relevance to the first analysis result, and reconstruction of the first medical image, and
wherein the first analysis result is visualized such that the first analysis result is distinguished based on quantitative information included in the first analysis result.

9. The medical image reading assistance apparatus of claim 1, wherein the first artificial neural network provides at least one of image segmentation of the first medical image, clinical diagnosis, and a quantitative measurement result of a segmented object within the first medical image as the first analysis result.

10. The medical image reading assistant apparatus of claim 1, wherein the first visualization format of the first medical image is generated based on the first analysis result including at least one of clinical findings, clinical diagnosis, or a quantitative measurement of a segmented object within the first medical image, wherein the first visualization format includes a segmentation result of the first medical image as a pre-processed result for the first analysis result.

11. The medical image reading assistance apparatus of claim 1, wherein the computing system further comprises a communication interface configured to transmit and receive data to and from the first artificial neural network disposed outside the computing system, and
wherein the at least one processor is further configured to acquire or receive the first analysis result obtained through the inference of the first artificial neural network for the first medical image via the communication interface.

12. A medical image reading assistance method that is performed by a computing system, wherein the computing system comprises at least one processor,
wherein the method comprises:
acquiring or receiving, by the at least one processor, a first analysis result obtained through inference of a first artificial neural network for a first medical image;
generating, by the at least one processor, a first visualization format, which is a representative visualization format of the first medical image, based on the first analysis result; and
visualizing, by the at least one processor, the first medical image based on the first visualization format,
wherein the computing system further comprises a second artificial neural network formed as an artificial neural network that has received a plurality of second visualization formats selected by a professional for a plurality of third analysis results obtained for a plurality of second medical images and has learned a function of generating visualization formats based on relevance between the plurality of third analysis results and the plurality of second visualization formats, and
wherein the generating comprises inputting, by the at least one processor, the first analysis result to the second artificial neural network, and controlling, by the at least one processor, the second artificial neural network so that the first visualization format is acquired through inference of the second artificial neural network.

13. The medical image reading assistance method of claim 12, further comprising, providing, by the at least one processor, a first user menu adapted to receive information about a user's approval for the first analysis result visualized based on the first visualization format of the first medical image.

14. The medical image reading assistance method of claim 13, further comprising, when the user does not approve the first analysis result, providing, by the at least one processor, a second user menu adapted to generate a second analysis result corresponding to the first analysis result for the first medical image independently of the first analysis result.

15. The medical image reading assistance method of claim 13, further comprising, when the user approves the first analysis result, storing, by the at least one processor, the first analysis result in a database in association with the first medical image.

16. The medical image reading assistance method of claim 15, wherein the storing comprises storing, by the at least one processor, the first analysis result in the database in association with the first medical image via a communication interface configured to transmit and receive data to and from the database disposed outside the computing system.

17. The medical image reading assistance method of claim 12, wherein the first visualization format comprises at least one of at least one view of the first medical image, at least part of the first medical image selected from the first medical image based on relevance to the first analysis result, and reconstruction of the first medical image, and
wherein the visualizing comprises visualizing the first analysis result so that the first analysis result is distinguished based on quantitative information included in the first analysis result.

18. The medical image reading assistance method of claim 1, wherein the first visualization format of the first medical image is generated based on the first analysis result including at least one of clinical findings, clinical diagnosis, or a quantitative measurement of a segmented object within the first medical image, wherein the first visualization format includes a segmentation result of the first medical image as a pre-processed result for the first analysis result.

19. The medical image reading assistance method of claim 12, wherein the acquiring or receiving comprises acquiring or receiving, by the at least one processor, the first analysis result via a communication interface configured to transmit and receive data to and from the first artificial neural network disposed outside the computing system.

* * * * *